US008975275B2

(12) United States Patent
Schulz et al.

(10) Patent No.: US 8,975,275 B2
(45) Date of Patent: Mar. 10, 2015

(54) USE OF CHEMOTHERAPEUTIC AGENTS

(75) Inventors: Hans-Herrmann Schulz, Köln (DE); Günther Schlimbach, Bergisch Gladbach (DE)

(73) Assignee: Bayer Innovation GmbH, Duesseldorf (DE)

( * ) Notice: Subject to any disclaimer, the term of this patent is extended or adjusted under 35 U.S.C. 154(b) by 494 days.

(21) Appl. No.: 10/168,441

(22) PCT Filed: Dec. 22, 2000

(86) PCT No.: PCT/EP00/13155
§ 371 (c)(1),
(2), (4) Date: Jun. 21, 2002

(87) PCT Pub. No.: WO01/45679
PCT Pub. Date: Jun. 28, 2001

(65) Prior Publication Data
US 2003/0045544 A1 Mar. 6, 2003

(30) Foreign Application Priority Data
Dec. 22, 1999 (DE) .................................. 199 62 470

(51) Int. Cl.
A61K 31/47 (2006.01)
A61K 31/4709 (2006.01)
A61K 31/4738 (2006.01)
A61K 8/49 (2006.01)
A61K 8/18 (2006.01)
A61Q 11/00 (2006.01)
A61K 9/00 (2006.01)
A61K 31/4745 (2006.01)
A61K 47/10 (2006.01)
A61K 47/38 (2006.01)
A61K 47/26 (2006.01)

(52) U.S. Cl.
CPC ............... A61K 9/0014 (2013.01); A61K 31/47 (2013.01); A61K 31/4709 (2013.01); A61K 31/4745 (2013.01); A61K 47/10 (2013.01); A61K 47/38 (2013.01); A61K 47/26 (2013.01); Y10S 514/90 (2013.01); Y10S 514/902 (2013.01)
USPC ........... 514/300; 514/900; 514/902; 514/310; 514/312; 514/253.08; 424/49; 424/423

(58) Field of Classification Search
USPC .......... 514/300, 311, 312; 500/300, 310, 312, 500/900, 902, 253.08; 424/49, 423
See application file for complete search history.

(56) References Cited

U.S. PATENT DOCUMENTS

| 4,399,134 A | 8/1983 | Ishikawa et al. | |
| 4,844,902 A | 7/1989 | Grohe | |
| 4,919,939 A * | 4/1990 | Baker | 424/493 |
| 4,965,262 A * | 10/1990 | Kametaka et al. | 514/230.2 |
| 4,980,470 A * | 12/1990 | Masuzawa et al. | 544/363 |
| 4,990,517 A | 2/1991 | Petersen et al. | |
| 5,164,402 A * | 11/1992 | Brighty | 514/300 |
| 5,563,138 A * | 10/1996 | Ueda et al. | 514/253.08 |
| 5,607,942 A * | 3/1997 | Petersen et al. | 546/200 |
| 5,620,700 A * | 4/1997 | Berggren et al. | 424/435 |
| 5,693,337 A | 12/1997 | Suzuki | |
| 6,262,071 B1 * | 7/2001 | Crabb et al. | 514/312 |
| 2002/0037260 A1 * | 3/2002 | Budny et al. | 424/49 |

FOREIGN PATENT DOCUMENTS

| CA | 2086914 | 7/1993 |
| EP | 0255926 | 2/1988 |
| EP | 274714 | 7/1988 |
| EP | 0286802 | 10/1988 |
| EP | 0908181 | 4/1999 |
| EP | 1408034 A1 | 4/2004 |
| JP | 63043668 | 2/1988 |
| JP | 63154621 | 6/1988 |
| JP | 63203629 | 8/1988 |
| JP | 1110628 | 4/1989 |
| JP | 2275820 | 9/1990 |
| JP | 2-275820 | 11/1990 |
| JP | 02275820 A | 11/1990 |
| JP | 5271229 | 10/1993 |
| JP | 6501010 | 2/1994 |
| JP | 6227964 | 8/1994 |
| JP | 06227964 A | 8/1994 |
| WO | 9204890 | 4/1992 |
| WO | 97/44034 A1 | 11/1997 |
| WO | 9744034 | 11/1997 |
| WO | 9907706 | 2/1999 |
| WO | 0018386 | 4/2000 |

OTHER PUBLICATIONS

American Dental Association http://www.ada.org/public/topics/plaque.asp, pp. 1-2 Oct. 2003.*
Lee et al., Western Journal of Medicine, "Quinolones: which generation for which microbe?", vol. 170, Jun. 1999, pp. 359-361.*
"Antibiotics and Dentistry: A Brief Review", Owens et al., Journal of Clinical Pediatric Dentistry, 1994, (Abstract enclosed).
"Antimicrobial Susceptibility of Anaerobic and Capnophilic Bacteria Isolated From Odontogenic Abscesses and Rapidly Progressive Periodontitis", Eick et al., International Journal of Antimicrobial Agents, 1999.
"Clinical and Microbiological Efficacy of Single Dose Cefuroxime Prophylaxis for Dental Surgical Procedures", Wahlmann et al., International Journal of Antimicrobial Agents, 1999.
"Antibiotic Sensitivity of Aerobic Microflora Isolated From Dental Root Canals", Kosowska et al., Med. Dosw. Mikrobiol. 1977, (Abstract Enclosed).
"Advances in Antimicrobial and Antineoplastic Chemotherapy", vol. 6-10. 1987.
Sobottka, Ingo, et al., "In Vitro Activity of Moxifloxacin against Bacteria Isolated from Odontogenic Abscesses." Antimicrobial Agents and Chemotherapy, Dec. 2002, 46 (12), p. 4019-4021.
Milazzo, I., et al. "Antibacterial activity of moxifloxacin against peridontal anaerobic pathogens involved in systemic infections." International Journal of Antimicrobial Agents 2002, 20 (6), p. 451-456.

(Continued)

Primary Examiner — Lezah Roberts
(74) Attorney, Agent, or Firm — Miles & Stockbridge PC

(57) ABSTRACT

The invention relates to the use of chemotherapeutic agents for the production of a medicament for the topical and/or local treatment of diseases caused by bacteria and/or for prophylaxis in humans or animals.

18 Claims, No Drawings

(56) References Cited

OTHER PUBLICATIONS

Eick, S., et al. "Efficacy of antibiotics to strains of peridontopathogenic bacteria within a single species of biofilm—an in vitro study." Journal of Clinical Peridontology 2004, 31, p. 376-383.

Bruce J. Paster, et al., "Bacterial Diversity in Human Subgingival Plaque", Journal of Bacteriology, (2001), p. 3770-3783, Jun. 2001.

Seiji Morita, Keni Otsubo, Minoru Uchida, Shigekatsu Kawabata, Hisashi Tamaoka and Takefumi Shimizu, Synthesis and Antibacterial Activity of the Metabolites of 9-Fluoro-6,7-dihydro-8-(4-hydroxy-1-piperidyl)-5-methyl-1-oxo-1H,5H-benzo[i,j]quinolizine-2carboxylic Acid (OPC-7251), Jul. 1990, 2027-2029, Chem. Pharm. Bull. 38 (7), Pharmaceutical Society of Japan.

Shigekatsu Kawabata, Hiroshi Masada, Hirokazu Wakebe, Kazunori Ohmori and Hisashi Tamaoka, Bacteriological Evaluation of OPC-7251, a New Pyridone Carboxylic Acid Antimicrobial Agent, Sep. 1989, 1179-1183, Chemotherapy vol. 37 No. 9.

Eick, Sigrun, et al., "In vitro antibacterial activity of fluoroquinolones against Porphyromonas gingivalis strains," Journal of Antimicrobial Chemotherapy (2004), 54, p. 553-556, Jul. 1, 2004.

Okazaki et al., "Enantioselective Disposition of Ofloxacin in Humans", Antimicrobial Agents and Chemotherapy, vol. 35, No. 10, Oct. 1991, p. 2106-2109.

Davies et al., "Importance of Chirality in Drug Therapy and Pharmacy Practice: Implications for Psychiatry", Advances in Pharmacy, vol. 1, No. 3, p. 242-252.

Takahashi et al., "Susceptibility of Actinobacillus actinomycetemcomitans to Six Antibiotics Decreases as Biofilm Matures", Journal of Antimicrobial Chemotherapy (2007) 59, 59-65.

Anderl et al., "Role of Nutrient Limitation and Stationary-Phase Existence in Klebsiella pneumoniae Bioflim Resistance to Ampicillin and Ciprofloxacin", Antimicrobial Agents and Chemotherapy, vol. 47, No. 4, Apr. 2003, p. 1251-1256.

Entenza et al., "Efficacies of Moxifloxacin, Ciprofloxacin, and Vancomycin Against Experimental Endocarditis Due to Methicillin-Resistant Staphylococcus aureus Expressing Various Degrees of Ciprofloxacin Resistance", Antimicrobial Agents and Chemotherapy, vol. 45, No. 11, Nov. 2001, p. 3076-3083.

Eng et al., "Bactericidal Effects of Antibiotics on Slowly Growing and Nongrowing Bacterial", Antimicrobial Agents and Chemotherapy, vol. 35, No. 9, Sep. 1991, p. 1824-1828.

Peterson et al., "Pharmacodynamics of Trovafloxacin and Levofloxacin Against Bacteroides fragilis in an In Vitro Pharmacodynamic Model", Antimicrobial Agents and Chemotherapy, vol. 46, No. 1, Jan. 2002, p. 203-210.

A. Dalhoff, "Pharmacodynamics of Fluoroquinolones", Journal of Antimicrobial Chemotherapy (1999) 43, Suppl. B., 51-59.

Hayakawa et al., "Synthesis and Antibacterial Activities of Optically Active Ofloxacin", Antimicrobial Agents and Chemotherapy, vol. 29, No. 1, Jan. 1986, p. 163-164.

Guentsch et al., "Moxifloxacin as an Adjunctive Antibiotic in the Treatment of Severe Chronic Periodontitis", vol. 9, No. 10, J. Periodontonol, Oct. 2008, p. 1894-1903.

Takahashi et al., "The effects of Tetracycline, Minocycline, Doxycycline and Ofloxacin on Prevotella intermedia Biofilm", Oral Microbiology Immunology, 2006 21: 366-371.

R. Albrecht, "Development of Antibacterial Agents of the Nalidixic Acid Type", Hauptdepartment Arzneimittelchemie, Schenng AG, Berlin, Bergkamen, 1977 p. 9-103.

Domagala et al., "Structure-Activity Relationships of the Quinolone Antibacterials in the New Millennium: Some Things Change and Some Do Not", Quinolone Antimicrobial Agents, 3rd Ed., 2003, ASM PRess, Washington, DC, p. 3-18.

Petersen et al., "The Synthesis and In Vitro and In Vivo Antibacterial Activity of Moxifloxacin (BAY 12-8039), a New Methoxyquinolone", Moxifloxacin in Practice, vol. 1, 1999, p. 13-26.

Yang et al., "Accumulation of Ciprofloxacin and Minocycline by Cultured Human Gingival Fibroblasts", Journal of Dental Research, 2002, 81: 836-840.

Qu et al., "Antibiotic Susceptibility of Coagulase-Negative Staphylococci Isolated from Very Low Birth Weight Babies: Comprehensive Comparisons of Bacteria at Different Stages of Biofilm Formation", Annals of Clinical Microbiology and Antimicrobials, 2010, 9:16, p. 1-12.

Flemmig et al., "Efficacy and Safety of Adjunctive Local Moxifloxacin Delivery in the Treatment of Periodontitis", J. Periodontol, Jan. 2011, p. 96-105.

Eick et al., "In Vitro Antibacterial Activity of Fluoroquinolones Against Porphyromonas gingivalis Strains", Journal of Antimicrobial Chemotherapy (2004) 54, 553-556.

Pfister et al., "Aktivitat von Chinolonen Gegenuber Oralen Anaeroben Und Kapnophilen Bakterien", Deutsche Zahnaerztliche Zeitschrift, 56 (2001) 3, p. 189-192.

Gascon et al., "Pharmacokinetics of Ofloxacin Enantiomers After Intravenous Administration for Antibiotic Prophylaxis in Biliary Surgery", J. Clin. Pharmacol. 2000 40: 869-874.

Agarwal et al., "In Vitro Efficacy of Ciprofloxacin and Gentamicin Against a Biofilm of Pseudomonas aeruginosa and Its Free-Living Forms", The National Medical Journal of India, vol. 18, No. 4, 2005, p. 184-186.

Dalhoff et al., "Effect of Quinolones Against Slowly Growing Bacteria", Chemotheraby 1995; 41: 92-99.

Dalhoff et al., "In Vitro Antibacterial Activity and Pharmacodynamics of New Quinolones", Eur J Clin Microbiol Infect Dis., (2003) 22:203-221.

John M. Domagala, "Structure-Activity and Structure-Side-Effect Relationships for the Quinolone Antibacterials", Journal of Antimicrobial Chemotherapy (1994) 33, 685-706.

Eick et al., "Efficacy of Antibiotics Against Periodontopathogenic Bacteria Within Epithelial Cells: An In Vitro Study", J Periodontol, Oct. 2004, vol. 75, No. 10, p. 1327-1334.

Eick et al., "Efficacy of Antibiotics to Strains of Periodontopathogenic Bacteria Within a Single Species Biofilm—An In Vitro Study", J. Clin Periodontol 2004: 31: 376-383.

Fujimoto et al., "In Vitro Antibacterial Activity of Dr-3355, the S-(−)-Isomer of Ofloxacin", Chemotherapy 1990: 36: 368-275.

Kimura et al., "Topical Chemotherapy in Human Periodontitis Using a New Controlled-Release Insert Containing Ofloxavin", J Periodont Res 1991; 26: 33-41.

Kleinfelder et al., Fluoroquinolones in the Treatment of Actinobacillus actinomycetemcomitans-Associated Periodontitis, Journal of Periodontology, 2000, vol. 71, p. 202-208.

Nichols et al., "The Role of Quinolones in Abdominal Surgery", Surgical Infections, Premier Issue, vol. 1, No. 1, 2000, p. 65-72.

Andrew B. Onderdonk, Ph.D, "Pharmacodynamics and Microbiology of Trovafloxacin in Animal Models of Surgical Infection", vol. 176 (Suppl 6a) Dec. 1998, p. 39-45.

Curriculum Vitae of Axel Dalhoff.

Darveau et al., "The Microbial Challenge in Periodontitis", Periodontology 2000, vol. 14, 1997, pp. 12-32, ISSN 0906-6713.

WHO Drug Information, vol. 21, No. 3, 2007; Recommended International Nonproprietary names for Pharmaceutical Substances (INN); List 58.

Rote Liste® Win Freigabadatum: Jul. 1, 2009, Druckdatum: Mar. 3, 2010, Seite 1, Nadixa® Creme.

P. Nenoff et al., "Activity of Nadifloxacin (OPC-7251) and Seven Other Antimicrobial Agents against Aerobic and Anaerobic Gram-Positive Bacteria Isolated from Bacterial Skin Infections", Chemotherapy 2004:50: pp. 196-201; DOI: 10.1159/00081032; published online: Sep. 23, 2004.

Zhang et al., "Besifloxacin, a novel fluoroquinolone antimicrobial agent, exhibits potent inhibition of pro-inflammatory cytokines in human THP-1 monocytes", Journal of Antimicrobial Chemotherapy (JAC), doi:10.1093/jac/dkm398, published Oct. 25, 2007.

Matsuzaki et al., "Antibacterial Activity of Nadifloxacin Against Staphylococcus and Propionibacterium Isolated From Patients With Dermatological Infections", The Japanes Journal of Antibiotics, vol. 59, Issue 4; p. 316(100)-320 (104), Aug. 2006.

Pihlstrom, et al., "Periodontal diseases", Lancet 2005, vol. 366, pp. 1809-1820, Nov. 19, 2005.

Limeres et al., "Empirical antimicrobial therapy for odontogenic infections", OOOOE, pp. 263-264, 2005.

(56) References Cited

OTHER PUBLICATIONS

Trombelli et al., "Periodontal diseases: current and future indications for local antimicrobial therapy", Oral Diseases (2003) 9 (Suppl. I), pp. 11-15, © 2003 Blackwell Munksgaard.
Wiles et al., "New Quinolone antibiotics: a survey of the literature from 2005 to 2010", Expert Opin. There. Patents (2010) 20(10); pp. 1295-1319.
Lynch et al., "New antibiotic agents and approaches to treat viofilm-associated infections", Expert Opin. Ther. Patents (2010) 20(10); pp. 1373-1387.
Furtado et al., "Overview perspective of bacterial resistance", Expert Opin. Ther. Patents (2010) 20(10): pp. 1273-1276.
Milazzo et al., "Antibacterial activity of moxifloxacin against periodontal anaerobic pathogens involved in systemic infections", International Journal of Antimicrobial Agents 20 (2002), pp. 451-456.
Sobottka et al., "In Vitro Activity of Moxifloxacin against Bacteria Isolated from odontongenic Abscesses", Antimicrobial Agents and Chemotherapy, vol. 46, No. 12; pp. 4019-4021; American Society for Microbiology 2002.
Keating et al., "Moxifloxacin a Review of its Use in the Management of Bacterial Infections", ADIS Drug Evaluation 2004; 64(20); pp. 2347-2377.
Heitz-Mayfield, "systemic antibiotics in periodontal therapy", Australian Dental Journal 2009; 54:(1 Suppl): S96-101, doi: 10.11111/j.1834-7819.
Posse et al., "Eficacia clinica del moxifloxacino en el trtamiento de abscesos odontogenicos submusosos", Semergen. 2006;32(2):pp. 58-62.
Socransky et al., "Dental biofilms: difficult therapeutic target", Periodontology 2000, vol. 28, pp. 12-55, ISSN 0906-6713, Munksgaard 2002.
Paju et al., "Oral biofilms, periodontitis, and pulmonary infections", Oral Diseases (2007) 13, pp. 508-512, doi:10.1111/j.1601.0825.2007.1410a.x; 2007 Blackwell Munksgaard.
Thomas et al., "In vitro activity of moxifloxacin compared to otherantimicrobials against streptococci isolated from iatrogenic oral bacteremia in Spain", Oral Microbiology Immunology 2004: 19: pp. 331-335, Blackwell Munksgaard 2004.
Jorgensen et al., "Periodontal antimicrobials-finding the right solutions", International Dental Journal (2005) 55, pp. 3-12, 2005 FDI/World Press.
Slots et al.,"Selection of antimicrobial agents in periodontal therapy", Journal of Periodontal Research, 37, pp. 389-398, ISSN 0022-3484, 2002 Blackwell Munksgaard Ltd.

Jung et al., "Biologically Based Treatment of Immature Permanent Teeth with Pulpal Necrosis: A Case Series", American Association of Endodontists, vol. 34, No. 7, doi: 10.1016/j.joen2008.03.023; pp. 877-887, Jul. 2008.
Tezel et al., "The gingival crevicular fluid ciprofloxacin level in subjects with gingivitis and periodontitis, and its effects on clinical parameters", Journal of Periodontal Research, vol. 40, pp. 395-400, doi10.111/j.1600-1675.2005.00820.x, Feb. 15, 2005, Blackwell Munksgaard Ltd.
Limeres et al., "Patients' Perception of Recovery After Third Molar Surgery Following Postoperative Treatment With Moxifloxacin Versus Amoxicillin and Clavulanic Acid: A Randomized, Double-Blind, Controlled Study", American Association of Oral and Maxillofacial Surgeons, Voume 67; pp. 286-291, doi.10.1016/j.joms.2008.06.061; 2009.
Olsen et al., "A Primer on Anaerobic Bacteria and Anaerobic Infections for the Uninitiated", Infection, vol. 27 No. 3, pp. 159-165, 1999.
Lee et al., "Quinolones: which generation for which microbe?", WJM, vol. 170, pp. 359-361, 1999.
Bautista, "Dental Injuries" (cont.), Extract-Medicinenet, 2011, pp. 1-3.
Dalhoff et al., "In vitro Activity of BAY 12-8039, a New 8-Methoxyquinolone", Microbiology, Chermotherapy vol. 42, pp. 410-425, 1996 S. Karger AG.
Xu et al., "Anti-adhesive effect of an acidic polysaccharide from *Aloe vera* L. var. chinensis (Haw.) Berger on the binding of *Helicobacter pylori* to the MKN-45 cell line", Journal of Pharmacy and Pharmacology, vol. 62, pp. 1753-1759, 2010 Royal Parmaceutical Society of Great Britain, ISSN 0022-3573 jphp_1181 1753.
Davis et al., "Single-Laboratory Validation of an NMR Method for the Determination of *Aloe vera* Polysaccharide in Pharmaceutical Formulations", Journal of AOAC International vol., 92, No. 6, pp. 1607-1616, 2009 Davis & Goux.
Vyas et. al., "Controlled and targeted drug delivery strategies towards intraperiodontal pocket diseases", Journal of Clinical Pharmacy and Therapeutics vol. 25, pp. 21-42, 2000 Blackwell Science Ltd.
Schaudinn et al., "Periodontitis: An Archetypical Biofilm Disease", J Am Dent Assoc; vol. 140, pp. 978-986, 2009.
Herrera et al., "Antimicrobial therapy in periodontitis: the use of systemic antimicrobials against the subgingival biofilm", J Clin Periodontol, vol. 35 (Suppl. 8); pp. 45-66, 2008 Blackwell Munksgaard.
Japanese Office Action and English translation of 2001-546418 (7 pages).

* cited by examiner

USE OF CHEMOTHERAPEUTIC AGENTS

This application claims the benefit of the earlier filed International Application No. PCT/EP00/13155, International Filing Date, Dec. 22, 2000, which designated the United States of America, and which international application was published under PCT Article 21(2) as WO Publication No. 01/45679 A2.

The present invention relates to the use of chemotherapeutic agents for the preparation of a medicament for the topical and/or local treatment of diseases caused by bacteria and/or for prophylaxis in humans or animals.

Bacteria can be the cause of a large number of diseases and can moreover impair wound healing. In the oral region, for example, tooth decay (caries) is caused by microbes specific to the mouth. Oral bacteria convert dietary carbohydrates to acids capable of dissolving the tooth enamel (enamelum) and dentin (dentinum). If the enamel surface is broken, the bacteria penetrate further into the underlying dentin. The radial dentinal tubules contain pulp processes, so partial or total infection and hence inflammation of the pulp occurs as the situation develops. The effect of inflammation of the pulp is to increase the congestion of blood. As the pulp is located in the rigid pulp cavity, it cannot expand and pain occurs. If the situation is left untreated, the consequences are necrosis of the pulp tissue and bacterial decomposition (gangrene). If the gangrenous matter is not removed, this is followed by inflammations outside the root tip. Granulomas, cysts, fistulation or abscesses may develop. Gas formation also exacerbates the pain at this stage.

Inflammation of the periodontium also involves bacteria. The periodontium consists of the gingiva, the annular ligament of the radius, the periodontal membrane and the intermediate Sharpey's fibres. An inflammation, periodontitis, can affect individual regions or the entire periodontium. Periodontitis, like caries, is caused by dental plaque at the margins of the gingiva, which hardens to tartar due to calcareous infiltrations. Bacteria living ill the plaque form metabolic products which cause periodontal disease. The gingiva gradually recedes and the periodontal membrane and alveolar bone begin to disintegrate. Sites of infection form in the surrounding tissue. The consequences are continued destruction of the bones and loosening of the teeth, which ultimately fall out. Damage in the oral region can also lead to diseases in other body organs.

Calcium hydroxide preparations or zinc oxide/clove oil (eugenol) are used for the treatment of caries profunda, both in the case of exposed pulp and when the dentin covering is still unbroken. An infected and necrotized pulp is removed as far as possible and the pulp cavity is filled with suitable root fillers. If the pulp is gangrenous, success can only be expected if the contaminated root canal system and the dentin near the canal can be disinfected. The main problems are the inaccessibility of the bacterially infected apical delta of the root canals, which is difficult to clean, and also the infected canal wall system, which has to be removed with considerable effort using instruments. A gangrene treatment is therefore normally a compromise solution and is wholly rejected by some schools, In principle, contraindications for a gangrene treatment are multirooted teeth and apical processes visible by X-ray. Extraction of the tooth is indicated in these cases. Periodontal diseases are treated by the removal of subgingival concrements. Other treatments use medicaments such as caustic agents, anti-inflammatories or vitamins.

Infections in the oral region are treated using antibiotics and chemotherapeutic agents with an antibacterial action, although these should only be administered after critical diagnosis. The preferred agents are antibiotics such as penicillin G or oral penicillins. Possible alternatives are erythromycin, lincomycin, clindamycin and, if appropriate, sulfonamides. The preferred agents in the case of mixed infections with Gram-negative microbes are broad-spectrum penicillins such as ampicillin, which can optionally be replaced by tetracyclines. Antibiotics and chemotherapeutic agents are always administered systemically. According to the prevailing school of thought, agents used for systemic chemotherapy should not be used as local antibiotics.

The current use of antimicrobial substances in dental medicine is described by B. M. Owens and N. J. Schuman (Journal of Clinical Pediatric Dentistry, 1994 (Winter), 18, 129-134; cited in Medline, A N 94331337). According to these authors, there ate two distinct categories of antimicrobial substances, namely naturally occurring substances from fungi (penicillins and cephalosporins), bacteria and actinomycetes (aminoglycosides), and their derivatives, which are called antibiotics, and compounds of synthetic origin (sulfanilamides and quinolones), which are called chemotherapeutic agents. The group of antibiotics which are important for dental medicine are penicillins, cephalosporins and aminoglycosides, as well as erythromycin. Because of their good efficacy, low costs and ease of use, these antibiotics are the preferred agents for many if not most odontogenous infections. The substances of synthetic origin are less valuable in dental medicine. According to the prevailing school of thought, they are frequently characterized by high costs, lack of efficacy and toxicity for the patient.

The sensitivity to antimicrobial agents of microbes which cause progressive periodontitis or odontogenous abscesses has been studied in vitro by S. Eick et al. (Int. J. Antimicrob. Agents, 1999, 12, 41-46) using modern antibiotics and chemotherapeutic agents, i.e. penicillin, amoxicillin, cefoxitin, clindamycin, doxyczycline, metronidazole and ciprofloxacin. The result was to recommend clindamycin for antimicrobial treatments.

Antibiotics have been used in dental medicine both systemically and topically to treat patients. U. Wahlmann et al. (Int. J. Antimicrob. Agents, 1999, 12, 253-256) have reported the effects of the systemic administration of cefuroxim ten minutes prior to a dental extraction. Bacteraemia occurred with a lower frequency in the group treated with cefuroxim than in the untreated group.

K. Kosowska and P. B. Heczko (Med. Dosw. Mikrobiol., 1977, 29, 101-106; cited in Chemical Abstracts, C A 88:69315) have reported the topical use of a variety of antibiotics. They treated infected teeth with various antibiotics, namely erythromycin, neomycin, chloramphenicol, colistin, nystatin or dexamethasone. The aerobic flora in the root canals was eliminated in about 55% of cases. However, the antibiotic resistance of the microorganisms isolated from the root canals after the treatment had been increased by the treatment. The resistance of Staphylococcus epidermis to erythromycin or methicillin was increased three-fold or two-fold, The majority of Staphylococcus aureus strains were resistant to erythromycin, chloramphenicol and penicillin.

The authors of the above literature references are all in agreement that the topical use of antibiotics and chemotherapeutic agents administered as sucking tablets, throat tablets, lozenges, styli, cones, powders or ointments are only of very little importance because of the frequent occurrence of increased resistance of the pathogens and because of the high sensitization rate. The therapeutic benefit is generally also limited in wounds with adequate external drainage, The substances used are scarcely absorbed, if at all, so their action cannot be expected to penetrate deeper into the tissue.

Accordingly, given the current state of the art in human and veterinary dental medicine, there is a great need for agents which have a high activity against the microbes occurring in the region of the mouth, teeth and jaws or in oral wounds, have a rapid bactericidal action, have a good local tolerability, elicit a low tendency to generate antibiotic resistance, can be applied topically and/or locally and hence are easy to administer, place a minimum systemic burden on the organism when administered topically/locally, and have a good tissue penetration, and whose use ensures the preservation of the damaged teeth.

Bacteria are also important in wound care. Wounds are tissue defects on the body surface and can be caused by injuries, operations, infections or pathophysiological processes. Wounds are dangerous inter alia because of possible infections due to penetration by pathogenic bacteria. Bacterial colonization of the wound can slow down or prevent the healing process or lead to other complications such as lymphangitis, sepsis or chronic infections.

Infected wounds must receive an antimicrobial treatment to control pathogenic microbes. Moreover, in a similar way to necrotic wounds, the wound must be cleaned to remove foreign bodies and cell detritus so that it can progress to the next healing phase. The treatment of an infected wound normally consists of a combined systemic and local approach where optionally antibiotics are used and a suitable dressing is applied which may itself have an antibacterial action. In many cases wound infections can be successfully treated by the administration of systemically active antibiotics, but the systemic administration of an antibiotic necessarily burdens the entire organism. This may be contraindicated in many cases, for example due to the patient's clinical situation, if the patient has many diseases or if an allergizing potential exists. It is advantageous in) such cases to apply the antibiotic topically and/or locally so that it can also be used in a higher local tissue concentration. Topical/local applications may also be favored by other factors, as in the case of certain hospital epidemiologies, or economic aspects such as the amounts needed, the prices of the medicaments and the costs due to side effects. However, the use of topical antibiotics is not generally recommended because this can lead to allergic reactions or to the formation of antibiotic-resistant species of bacteria. It is therefore regarded as particularly important to limit the use of topical antibiotics.

Nowadays a local antibiotic treatment is used only for superficial skin infections because the antibiotic can act directly on the pathogens. A local application is unsuccessful in the case of deep skin infections because the antibiotics do not penetrate the intact skin. There are three preferred groups of local antibiotics in use today. These axe polypeptides such as bacitracin, tyrothricin, colistin and polymyxin B, or aminoglycosides such as neomycin, kanamycin and paromycin or mupirocin. However, with the presence of local or systemic toxicity and the danger of the secondary development of bacterial resistance, local antibiotics should only be used with great restraints In local therapies with gyrase inhibitors, incorporation into plastic materials has been proposed as a possible clinical application in addition to conventional forms of administration such as eye drops, ear drops, instillation solutions, powders and healing ointments (W. Stille, Fortschritte der antimikrobiellen und antineoplastishen Chemotherapie (Advances in antimicrobial and antineoplastic chemotherapy), vol. 6-10, 1987, pp. 1575-1583).

Accordingly, given the current state of the art, there is also a need in human and veterinary medicine for topically and/or locally applicable agents with an antibiotic action which have a high activity against the microbes occurring in wounds, have a rapid bactericidal action, have a good local tolerability, elicit a low tendency to generate antibiotic resistance, are easy to administer by topical and/or local application, place a minimum systemic burden on the organism when administered topically/locally, have a good tissue penetration, are also suitable for the treatment of deep infections and additionally accelerate the wound healing process.

It has now been found, surprisingly, that certain chemotherapeutic agents, administered locally and/or topically, have an extremely positive effect in a variety of ways on the treatment of diseases caused by bacteria in the oral region of humans and animals, for example dental and periodontal diseases, and on wound healing. Medicaments which contain these chemotherapeutic agents can be used successfully in dental medicine against microbes encountered in the soft tissue and/or hard tissue, where they lead to inflammations. The medicaments are generally suitable for the local treatment of endodontal syndromes such as pulpitis due to carious diseases, for the prophylaxis of dentin wounds, for the topical treatment of the infected root canal and the periapical tissue, and also for the topical treatment of periodontal diseases, of osseomucosal wounds with disturbed wound healing, for example after dental extraction, and of soft tissue infections. Such diseases are caused by bacteria in the hard dental tissue, for example in the case of infections in the crown and root dentin, in the dentin inside the root canal and in the root cement in the apical region of the root of the tooth. Also included are bacterial infections of the jawbone and alveolar bone, They are also to be understood as including infections in the soft tissues, for instance in the pulp, in the periodontal tissue, in the gingival mucosa, in the alveolar mucosa, in the labial and buccal mucosa, in the palatine mucosa and in the periglottis. It has further been found, surprisingly, that the use of these chemotherapeutic agents in human and veterinary medicine also has a positive effect in a variety of ways on the treatment and prophylaxis of wounds. This was shown in the treatment of different forms of wounds, for example in surgical infections such as postoperative or posttraumatic wound infections, in perioperative prophylaxis, in infected burns, in hand infections, in postoperative sepsis, in infected ulcers and gangrenes and in skin infections such as acute and chronic bacterial skin infections, secondarily infected dermatoses or acne and rosacea. These lists are examples and do not imply a limitation to the areas mentioned.

These diseases can be treated according to the invention by the local and/or topical application of chemotherapeutic agents.

In terms of the invention, chemotherapeutic agents are derivatives of quinolone-carboxylic acid or naphthyridonecarboxylic acid of general formula (I):

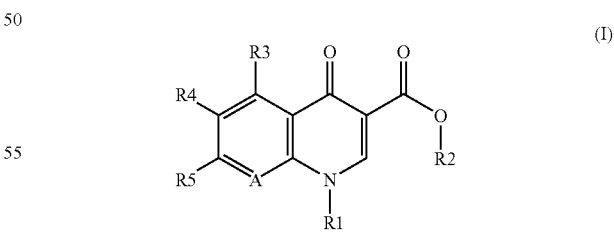

in which:

A is CH, C-halogen, C—CH$_3$, C—CN, C—OCH$_3$, C—OCHF$_2$ or N,
R1 is C$_1$–C$_5$-alkyl, C$_1$–C$_5$-alkenyl, 2-fluoroethyl, cycloalkyl, bicycloalkyl, 2-fluorocyclopropyl, 1-oxetan-3-yl, methylamino, optionally substituted phenyl or pyridyl, or A and R1 together form the group C—O—CH$_2$—CH(CH$_3$)—, R2 is hydrogen or C₁–C₃-alkyl optionally substituted by hydroxyl, halogen or amino,
R3 is hydrogen, halogen, methyl, amino or NH—NH₂,
R4 is hydrogen, halogen or amino, and
R5 is an optionally monosubstituted or polysubstituted mono-, bi- or tricyclic alicycle which is saturated or has at least one double bond and which optionally has at least one heteroatom in the ring system, or an aromatic mono-, bi- or tricycle optionally having at least one heteroatom, and/or 4H-4-oxoquinolizines of general formula (II):

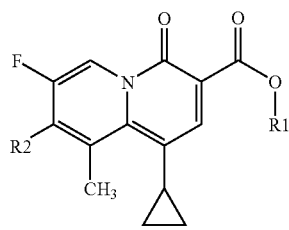

(II)

in which;

R1 is hydrogen or C₁–C₃-alkyl, and
R2 is an optionally monosubstituted or polysubstituted mono-, bi- or tricyclic alicycle which is saturated or has at least one double bond and which optionally has at least one heteroatom in the ring system, or an aromatic mono-, bi- or tricycle optionally having at least one heteroatom, and/or their corresponding hydrates and/or their corresponding physiologically compatible acid addition salts and/or optionally the corresponding physiologically compatible salts of the carboxylic acids on which they are based, i.e. the compounds of general formula (I) in which R2 is H and/or the compounds of general formula (II) in which R1 is H, and/or corresponding enantiomers and/or corresponding diastereomers and/or corresponding racemates and/or corresponding mixtures of at least two of the above-mentioned compounds.

When administered topically and/or locally, these compounds have a beneficial action in the treatment of diseases caused by bacteria in the oral region of humans and animals, especially in the treatment of pulpitis, including infections of the root canal and the periapical tissue, periodontal diseases and odontogenous or oral soft tissue infections, in the prophylaxis of dentin wounds, in the treatment of forms of wounds in humans and animals arising from surgical infections such as postoperative or posttraumatic wound infections, in perioperative prophylaxis, in infected burns, in hand infections, in postoperative sepsis, in infected ulcers and gangrenes, in acute and chronic bacterial skin infections, secondarily infected dermatoses or acne and rosacea, and in general for the acceleration of wound healing in humans and animals.

It is preferred to use at least one of these compounds to prepare a pharmaceutical product, especially a medicament, for the topical and/or local treatment of diseases caused by bacteria or for the acceleration of wound healing.

It is preferred to use the compounds of formula (I) in which

A is CH, CF, CCl, CBr, C—CH₃, C—CN, C—OCH₃, C—OCHF₂ or N,
R1 is ethyl, 1,1-dimethylethyl, 1-ethenyl, 1,1-dimethylprop-2-ynyl, 2-fluoroethyl, cyclopropyl, bicyclo(1.1.1)pent-1-yl, 2-fluorocyclopropyl, 1-oxetan-3-yl, methylamino, 4-fluorophenyl, 2,4-difluorophenyl, 5-amino-2,4-difluorophenyl, 5-fluoropyridin-2-yl or 6-amino-3,5-difluoropyridin-2-yl, or A and R1 together form the group C—O—CH₂—CH(CH₃)—, the —CH(CH₃)— part of this group being bonded to the nitrogen atom of the heterocycle,
R2 is hydrogen, methyl or ethyl,
R3 is hydrogen, F, Cl, Br, methyl, amino or NH—NH₂,
R4 is hydrogen, F or amino, and
R5 is optionally monosubstituted or polysubstituted cyclopropyl, azetidinyl, pyrrolidinyl, piperidinyl, piperazinyl, morpholinyl, phenyl, pyrrolyl, pyridyl or imidazolyl, it optionally also being possible for at least two substituents to be coupled together, and/or the compounds of formula (II) in which R1 is hydrogen, and
R2 is optionally monosubstituted or polysubstituted cyclopropyl, azetidinyl, pyrrolidinyl, piperidinyl, piperazinyl or morpholinyl, it optionally also being possible for at least two substituents to be coupled together.

It is particularly preferred to use the compounds of formula (I) in which

A is CH, CF, CCl, C—CN, C—OCH₃ or N,
R1 is cyclopropyl, 2-fluorocyclopropyl, 4-fluorophenyl or 2,4-difluorophenyl, or A and R1 together form the group C—O—CH₂—CH(CH₃)—, the —CH(CH₃)— part of this group being bonded to the nitrogen atom of the heterocycle,
R2 is hydrogen,
R3 is hydrogen or amino,
R4 is hydrogen or F, and
R5 is optionally monosubstituted or polysubstituted pyrrolidinyl, piperidinyl, piperazinyl or morpholinyl, it optionally also being possible for at least two substituents to be coupled together.

It is very particularly preferred to use the compounds of formula (I) in which

A is CH, CF, CCl, C—OCH₃ or N,
R1 is cyclopropyl or 2,4-difluorophenyl, or A and R1 together form the group C—O—CH₂—CH(CH₃)—, the CH(CH₃)— part of this group being bonded to the nitrogen atom of the heterocycle,
R2 is hydrogen,
R3 is hydrogen or amino,
R4 is hydrogen or F, and
R5 is pyrrolidinyl, piperidinyl, piperazinyl, morpholinyl or 3-azabicyclo(3.1.0)hexyl optionally substituted by amino, methyl, aminomethyl and/or methoxyimino, or piperidinopyrrolidinyl.

Bi- or tricyclic alicycles or aromatic bi- or tricycles R5 in general formula (I) and R2 in general formula (II) are also understood as including fused ring systems which can optionally have at least one double bond and/or at least one heteroatom in the ring system.

Examples of radicals R5 in the compounds of formula (I) are 1-aminocyclopropyl, 3-hydroxyazetidin-1-yl, 3-aminioazetidin-1-yl, 3-methylaminoazetidin-1-yl, 3-amino-2-methylazetidin-1-yl, 3-amino-3-methylazetidin-1-yl, 3-amino-2,3-dimethylazetidin-1-yl, 3-aminopyrrolidin-1-yl, 3-(2-amino-1-oxopropyl)amino-1-pyrrolidin-1-yl, 3-norvalylnorvalylamino-1-pyrrolidin-1-yl, 3-amino-3-fluoromethylpyrrolidin-1-yl, 3-amino-4-methylpyrrolidin-1-yl, 3-amino-4-fluoromethylpyrrolidin-1-yl, 4-amino-2-methylpyrrolidin-1-yl, 4-amino-3,3-dimethyl-1-pyrrolidin-1-yl, 3-amino-3-phenylpyrrolidin-1-yl, 3-amino-4-cyclopropylpyrrolidin-1-yl, 3-aminomethylpyrrolidin-1-yl, 3-ethylaminomethylpyrrolidin-1-yl, 3-(1-aminoethyl)-1-pyrrolidin-1-yl, 3-(1-amino-1-methylethyl)pyrrolidin-1-yl, 3-aminomethyl-3-methylpyrrolidin-1-yl, 3-aminomethyl-3-fluoromethylpyrrolidin-1-yl, 3-aminomethyl-4-methylpyrrolidin-1-yl, 3-aminomethyl-4-trifluoromethylpyrrolidin-1-yl, 3-aminomethyl-4-chloropyrrolidin-1-yl, 3-aminomethyl-4-methoxyiminopyrrolidin-1-yl, 3-(2-methyl-1H-imidazol-1-yl)pyrrolidin-1-yl, 3-(4-methyl-1,2,3-triazol-1-yl)pyrrolidin-1-yl, 3-methylaminopiperidin-1-yl, 4-hydroxypiperidin-1-yl, 4-hydroxyiminopiperidin-1-yl, piperazin-1-yl, 3-methyl-1-piperazinyl, 4-methylpiperazin-1-yl, 4-ethylpiperazin-1-yl, 4-acetylpiperazin-1-yl, 4-(5-methyl-2-oxo-1,3-dioxol-4-yl)methylpiperazin-1-yl, 4-(3-carboxy-1-oxopropyl)piperazin-1-yl, 3,5-dimethylpiperazin-1-yl, 2,4,5-trimethylpiperazin-1-yl, 3,4,5-trimethylpiperazin-1-yl, 2-aminomethylmorpholin-4-yl, 2-dimethylaminomethylmorpholin-4-yl, 3-methylaminomethylmorpholin-4-yl, 7-amino-5-azaspiro(2.4)heptan-5-yl, 8-amino-6-azaspiro(3.4)octan-6-yl, 6-amino-3-azabicyclo(3.1.0)hexan-3-yl, 6-alanylalanylamino-3-azabicyclo(3.1.0)hexan-3-yl, 6-amino-1-methyl-3-azabicyclo(3.2.0)heptan-3-yl, 6-methyl-2,5-diazabicyclo-(2.2.1)heptan-2-yl, 2,5-diazabicyclo(2.2.1)heptan-2-yl, 8-methyl-3,8-diazabicyclo-(3.2.1)octan-3-yl, 5-amino-2-aza-2-spiro[4.4]nonyl, 1-aminomethyl-8-aza-8-bicyclo-[4.3.0]nonyl, 5-aminomethyl-7-aza-2-oxo-7-bicyclo[3.3.0]octyl, 1-aminomethyl-7-aza-3-oxo-7-bicyclo[3.3.0]octyl, 2,7-diaza-7-bicyclo[3.3.0]octyl, 3,7-diaza-3-bicyclo[3.3.0]octyl, 2,8-diaza-8-bicyclo[4.3.0]nonyl, 5,8-diaza-2-oxo 8-bicyclo[4.3.0]nonyl, 3,8-diaza-8-bicyclo[4.3.0]nonyl, 2,7-diaza-7-bicyclo[4.3.0]nonyl, 3,9-diaza-9-bicyclo[4.3.0]nonyl, 3,9-diaza-3-bicyclo[4.3.0]nonyl, 7-amino-3-aza-3-bicyclo[4.1.0]heptyl, 7-amino-5-azaspiro[2.4]hept-5-yl or 7-methylamino-5-azaspiro[2.4]hept-5-yl, 2,7-diaza-2-bicyclo[3.3.0]octyl, 4-amino-1,3-dihydro-2H-isoindol-2-yl, 3,4-dihydro-2(1H)-isoquinolinyl, hexahydropyrrolo[3,4-b]pyrrol-5(1H)-yl, octahydro-6H-pyrrolo[3,4-b]pyridin-6-yl, hexahydropyrrolo[3,4-b]-1,4-oxazin-6(2H)yl, 2,3-dihydro-1-methyl-1H-isoindol-5-yl, pyridin-4-yl, 2,6-dimethylpyridin-4-yl, 1H-pyrrol-1-yl or 1H-imidazol-1-yl.

Examples of radicals R2 in the compounds of formula (II) are azetidin-1-yl, 2hydroxymethylazetidin-1-yl, 2-aminomethylazetidin-1-yl, pyrrolidin-1-yl, isoxazolin-1-yl, 2-methylpyrazolidin-1-yl, 3-hydroxypyrrolidin-1-yl, 3-carboxypyrrolidin-1-yl, 3-aminopyrrolidin-1-yl, 3-aminomethylpyrrolidin-1-yl, 3-methylaminopyrrolidin-1-yl, 3-ethylaminopyrrolidin-1-yl, 3-fluoroethylaminopyrrolidin-1-yl, 3-trifluoroethylaminopyrrolidin-1-yl, 3-methoxyethylaminopyrrolidin-1-yl, 3-(N-methyl-N-cyclopropylamino)pyrrolidin-1-yl, 3-amino-4-cyclopropylpyrrolidin-1-yl, 4-methyl-3-methylaminopyrrolidin-1-yl, 3-cyclopropylamino-4-methylpyrrolidin-1-yl, 3-(1-amino-8-aza-8-bicyclo[4.3.0]nonyl, 3-aminomethylpyrrolidin-1-yl, 3-aminomethyl-3-trifluoromethylpyrrolidin-1-yl, 5-amino-2-aza-2-spiro[4.4]nonyl, 1-aminomethyl-8-aza-8-bicyclo[4.3.0]nonyl, 5-aminomethyl-7-aza-2-oxo-7-bicyclo[3.3.0]octyl, 1-aminomethyl-7-aza-3-oxo-7-bicyclo[3.3.0]octyl, 2,7-diaza-7-bicyclo[3.30]octyl, 3,7-diaza-3-bicyclo[3.3.0]octyl, 2,8-diaza-8-bicyclo[4.3.0]nonyl, 5,8-diaza-2-oxo-8-bicyclo[4.3.0]nonyl, 3,8-diaza-8-bicyclo[4.3.0]nonyl, 2,7-diaza-7-bicyclo[4.3.0]-nonyl, 3,9-diaza-9-bicyclo[4.3.0]nonyl, 2,7-diaza-2-bicyclo[3.3.0]octyl, piperidin-1-yl, 3-aminopiperidin-1-yl, 3-amino-4-metylpiperidin-1-yl, 3,9-diaza-3-bicyclo-[4.3.0]nonyl, 7-amino-3-aza-3-bicyclo[4.1.0]heptyl, 7-amino-5-azaspiro[2.4]hept-5-yl or 7-methylamino-5-azaspiro[2.4]hept-5-yl.

Examples of compounds of formula (I) or formula (II) are 1-cyclopropyl-6-fluoro-1,4-dihydro-8-methoxy-7-[3-(methylamino)-1-piperidinyl]-4-oxo-3-quinoline-carboxylic acid (balofloxacin), 8-chloro-1-cyclopropyl-6-fluoro-1,4-dihydro-7-[(4aS,7aS)-octahydro-6H-pyrrolo[3,4-b]pyridin-6-yl]-4-oxo-3-quinolinecarboxylic acid monohydrochloride (BAY Y3118), 1-cyclopropyl-6-fluoro-8-difluoromethoxy-1,4-dihydro-7-((3S)-methyl-1-piperazinyl)-4-oxo-3-quinolinecarboxylic acid hydrochloride (caderofloxacin), 1-cyclopropyl-6-fluoro-1,4-dihydro-4-oxo-7-(1-piperazinyl)-3-quinolinecarboxylic acid (ciprofloxacin), 7-(3-amino-1-pyrrolidinyl)-8-chloro-1-cyclopropyl-6-fluoro-1,4-dihydro-4-oxo-3-quinolinecarboxylic acid (clinafloxacin), (1α,5α,6β)-(+)-7-(6-amino-1-methyl-3-azabicyclo[3.2.0]hept-3-yl)-1-cyclopropyl-6-fluoro-1,4-dihydro-4-oxo-1,8-naphthyridine-3-carboxylic acid (ecenofloxacin), 1-ethyl-6-fluoro-1,4-dihydro-4-oxo-7-(1-piperazinyl)-1,8-naphthyridine-3-carboxylic acid (enoxacin), 1-cyclopropyl-7-(4-ethyl-1-piperazinyl)-6-fluoro-1,4-dihydro-4-oxo-3-quinolinecarboxylic acid (enrofloxacin), 6-fluoro-1-(5-fluoro-2-pyridinyl)-1,4-dihydro-7-(4-methyl-1-piperazinyl)-4-oxo-3-quinolinecarboxylic acid (fandofloxacin), 6,8-difluoro-1-(2-fluoroethyl)-1,4-dihydro-7-(4-methyl-1-piperazinyl)-4-oxo-3-quinolinecarboxylic acid (fleroxacin), 1-cyclopropyl-6-fluoro-1,4-dihydro-8-methoxy-7-(3-methyl-1-piperazinyl)-4-oxo-3-quinolinecarboxylic acid (gatifloxacin), 7-[(4Z)-3-(aminomethyl)-4-(methoxyimino)-1-pyrrolidinyl]-1-cyclopropyl-6-fluoro-1,4-dihydro-4-oxo-1,8-naphthyridine-3-carboxylic acid (gernifloxacin), 1-cyclopropyl-6-fluoro-1,4-dihydro-5-methyl-7-(3-methyl-1-piperazinyl)-4-oxo-3-quinolinecarboxylic acid (grepafloxacin), (3S)-9-fluoro-2,3-dihydro-3-methyl-10-(4-methyl-1-piperazinyl)-7-oxo-7H-pyrido[1,2,3-de]-1,4-benzoxazine-6-carboxylic acid (levofloxacin), 1-ethyl-6,8-difluoro-1,4-dihydro-7-(3-methyl-1-piperazinyl)-4-oxo-3-quinolinecarboxylic acid (lome-floxacin), 1-cyclopropyl-6-fluoro-1,4-dihydro-8-methoxy-7-[(4aS,7aS)-octahydro-6H-pyrrolo[3,4-b]pyridin-6-yl]-4-oxo-3-quinolinecarboxylic acid (moxifloxacin), 9-fluoro-6,7-dihydro-8-(4-hydroxy-1-piperidinyl)-5-methyl-1-oxo-1H,5H-benzo[ij]quinolizine-2-carboxylic acid (nadigoxacin), 1-ethyl-6-fluoro-1,4-dihydro-4-oxo-7-(1-piperazinyl)-3-quinolinecarboxylic acid (norfloxacin), 9-fluoro-2,3-dihydro-3-methyl-10-(4-methyl-1-piperazinyl)-7-oxo-7H-pyrido[1,2,3-de]-1,4-benzoxazine-6-carboxylic acid (ofloxacin), 5-amino-7-[(7S)-7-amino-5-azaspiro[2.4]hept-5yl]-1-cyclopropyl-6-fluoro-1,4-dihydro-8-methyl-4-oxo-3-quinolinecarboxylic acid (olamufloxacin), (3S)-10-(1-aminocyclopropyl)-9-fluoro-2,3-dihydro-3-methyl-7-oxo-7H-pyrido[1,2,3-de]-1,4-benzoxazine-6-carboxylic acid (pazufloxacin), 1-ethyl-6-fluoro-1,4-dihydro-7-(4-methyl-1-piperazinyl)-4-oxo-3-quinolinecarboxylic acid (pefloxacin), 6-fluoro-1-methyl-7-[4-[(5-methyl-2-oxo-1,3-dioxol-4-yl)methyl]-1-piperazinyl]-4-oxo-1H,4-[1,3]thiazeto[3,2-a]quinoline-3-carboxylic acid (prulifloxacin), 1-ethyl-1,4-dihydro-4-oxo-7-(4-pyridinyl)-3-quinolinecarboxylic acid (rosoxacin), 7-[(7S)-7-amino-5-azaspiro[2.4]hept-5-yl]-8-chloro-6-fluoro-1-[(1R,2S)-2-fluorocyclopropyl]-1,4-dihydro-4-oxo-3-quinolinecarboxylic acid (sitafloxacin), 5-amino-1-cyclopropyl-7-[(3R,5S)-3,5-dimethyl-1-piperazinyl]-6,8-difluoro-1,4-dihydro-4-oxo-3-quinolinecarboxylic acid (sparfloxacin), 7-(3-amino-1-pyrrolidinyl)-1-(2,4-difluorophenyl)-6-fluoro-1,4-dihydro-4-oxo-1,8-naphthyridine-3-carboxylic acid (tosufloxacin) or 7-(1α,5α,6α-6-amino-3-azabicyclo[3.1.0]hex-3-yl)-1-(2,4-difluorophenyl)-6-fluoro-1,4-dihydro-4-oxo-1,8-naphthyridine-3-carboxylic acid (trovafloxacin).

If corresponding physiologically compatible acid addition salts of the compounds of general formula (I) and/or of general formula (U) are used, these can preferably be selected from the group comprising hydrochloride, hydrobromide, methanesulfonate and toluenesulfonate. If corresponding physiologically compatible salts of the carboxylic acids on which said compounds are based are used, these can preferably be selected from the group comprising alkali metal salts, alkaline earth metal salts, ammonium salts, guanidinium salts and silver salts. It is also possible to use mixtures of at least two of the above-mentioned physiologically compatible salts.

The above-mentioned compounds of formula (I) or formula (II) are known and can be prepared by conventional processes familiar to those skilled in the art. It is also known that the compounds of formula (I) or formula (II) have an antibiotic action and have an antibacterial spectrum against Gram-positive and Gram-negative microbes. It is also known that it is possible to use the compounds of formula (I) or formula (II) for the systemic treatment of diseases which can be caused by Gram-negative, Gram-positive or bacterioid microorganisms. It is also known that ciprofloxacin can be used in topical form in ophthalmology.

The compounds of general formula (I) or of general formula (II) can be used for the topical and/or local treatment of a variety of diseases caused by bacteria and for prophylaxis in humans and animals.

The compounds of formula (I) or formula (II) can be used particularly in dental medicine and/or for improving wound healing in general medicine or veterinary medicine. The uses according to the invention of the compounds of formula (I) or formula (II) preferably involve a) endodontal treatments such as the topical treatment of pulpitis due to carious diseases, the prophylaxis of dentin wounds or the topical treatment of the infected root canal and the periapical region, b) the topical treatment of periodontal diseases, c) the topical treatment of oral osseomucosal wounds with disturbed wound healing, or prophylactic treatment, for example after extractions, cystectomy or incisions due e.g. to phlegmons or parulides, d) the topical and/or local treatment of postoperative or posttraumatic wound infections, e) perioperative prophylaxis, f) infected burns, g) hand infections, h) postoperative sepsis, i) infected ulcers and gangrenes, j) acute and chronic bacterial skin infections, k) secondarily infected dermatoses, l) acne and rosacea, or m) mucosal ulcerations.

Preferred uses according to the invention ate described below using the areas of dental medicine and wound healing as examples.

Topical Treatment of Pulpitis Due to Carious Diseases

The particular problems associated with treatment of the pulp are the small lymph supply, its position as a terminal organ with a small collateral circulation, and the influence of external stimuli given its location in a rigid, inflexible cavity. In the case of carious defects, the microorganisms advance in the direction of the pulp, cross the enamel-dentin interface and soften the dentin cone. If the carious process reaches half of tie total dentin layer, the pulp is already histologically modified, even though clinical symptoms are often stilt absent. If the caries advances further without penetrating the remainder of the dentin covering, symptoms of pulpitis are normally experienced. If the caries reaches the pulp, different histopathological forms arise. These consequences of the carious process are attributable to the fact that dentin has radial channels, called dentinal tubules, running through it, said tubules containing pulp processes. These processes of the dentinogenic cells (odontoblasts), which are located at the periphery of the pulp, serve inter alia to conduct stimuli. It is known that the microorganisms and their toxins follow the dentinal tubules. If the caries extensively penetrates the dentin layer or reaches the pulp, the condition is referred to as caries profunda.

The particular problem associated with the diagnosis of a pulp disease is that the histological and clinical pictures are often quite different. As pain is sensed and interpreted differently by different patients, there is always the risk of a false diagnosis. The pulp infection has often progressed Other than is clinically ascertainable. Under the conventional treatment, there is then the danger of residual microbes being left behind.

In the conventional treatment of caries normally used today, the carious matter is first removed. Then the cavity is disinfected, for example with hydrogen peroxide, and, depending on the degree of pulp inflammation, is indirectly or directly capped. This means that a thin residual dentin covering is left untouched or the exposed pulp is coated with a medicaments This is done using either calcium hydroxide or zinc oxide/eugenol. Both medicaments are strongly alkaline, have an antibacterial action and induce caustic necrosis in a local region of the pulp. This has the effect of building secondary dentin, depending on the extent of the previous damage and the resistance situation. The capping agent is covered with a reliner, for example zinc phosphate cement. In the same session or at a later time, the definitive filling is prepared, for example with a composite cement. In cases of particular pain symptoms or where the pulp no longer reacts to external stimuli, it is assumed that the pulp can no longer regenerate or that it is dead. In these cases the pulp is removed and a root treatment is carried out.

The topical treatment of infected dentin and pulpitis with antibiotics has hitherto been described in the scientific literature as unsuccessful. As the main argument against this method of treatment, it is stated that the microbes in question (anaerobes and aerobes) were only dealt with to a very limited extent by the antibiotics tested, It was further established that the antibiotics tested earlier for these indications generally have only a bacteriostatic action and not a bactericidal action. This allows resistant microbes to get out of control and hypersensitivity reactions against a particular antibiotic can be triggered.

It has now been found, surprisingly, that, when applied topically and/or locally to the periodontal interstice in dentistry, the antibiotics of formula (I) or formula (II) completely control the bacteria occurring in odontogenous infections, and additionally that the disadvantages of the conventional treatment described above do not arise. It has father been found that the compounds of formula (I) or formula (II) have a high tissue penetration in the odontogenous region. It has also been found that, under treatment with the compounds of formula (I) or formula (II), the microbes of odontogenous infections have no tendency to develop resistance. This is of great importance because, for example in the case of caries profunda, it is always necessary to decide whether softened residual dentin can be left over the pulp. By virtue of complete elimination of the microbes present, there is now a novel method of treatment wherein a thin softened dentin covering can be left if the compounds of formula (I) or formula (II) are used. This method of treatment makes it possible to free infected dentin layers of microbes and to stop pulp infections. This means that pain reactions are eliminated and pulp infections are to a certain extent cured. The pulp remains vital.

The topical application of the compounds of formula (I) or formula (II) followed the removal of the carious dentin. The compounds of formula (I) or formula (II) were applied for example in aqueous solution, in a form of gelatinous consistency or on an inert carrier, for example by means of a cotton wool plug. The overlying cavity was occluded with a cement to seal the margins. The cotton wool plug was left in the cavity for three to six days. The compounds of formula (I) or formula (II) can be used in concentrations of 0.005 mg/ml to 200 mg/ml, Preferred concentrations are those ranging from 0.5 mg/ml to 150 mg/ml and particularly preferred concentrations are those ranging from 10 to 100 mg/ml.

Surprisingly, it was observed in a large number of cases that the action of compounds of formula (I) or formula (II) even resulted in a regeneration of the pulp tissue. This was shown by the fact that, after extirpation of the infected and inflamed pulp, the nerve needle could be introduced as far as the foramen physiologicum. About two weeks after the topical application of a compound of formula (I) or formula (II), a burgeoning of fresh pulp tissue was observed which was characterized in that the vertical canal volume was found to have shrunk when inspected with instruments, and fresh pulp tissue had grown out again into the canal in the direction of the crown. This pulp tissue was vital.

Prophylaxis of Dentin Wounds

In the treatment of carious defects or after the preparation of dentin surfaces to receive e.g. fillings, inlays, onlays, crowns or bridges, dentinal tubules which are directly connected to the pulp, and hence provide access to the pulp, are cut. Each prepared dentin surface is covered by an organic layer and preparation residues (smear layer). If the preparatory work is also carried out in dentin modified by caries, said surface normally contains microorganisms. The usual practice is to flush the dentin wound with hydrogen peroxide and then carefully dry it with the air syringe. Even when the cavity walls are 'hard to the probe' after removal of the caries and preparation of the cavity, and the cavity has been treated with disinfectants, there is still the possibility that microbes have already advanced further in the dentinal tubules in the direction of the pulp and are unreachable by disinfectants. This can cause dentin hypersensitivities and subsequently secondary caries.

It has now been found that the prophylactic topical use of the compounds of formula (I) or formula (II) after every preparation associated with carious defects in the dentin region can also destroy microbes which have advanced well into the dentinal tubules, and that said compounds thus have an advantageous effect on the tooth-preserving procedures. For this reason, after removal of the carious regions, the compounds of formula (I) or formula (II) are applied to the prepared cavities and rubbed in. Said compounds are applied in the form of solutions, gels or suspensions to form a local depot with an antibiotic action before the reliner is placed on and/or in the fundament of the inlays, onlays, crowns or bridges. This results in the effective destruction of the residual pathogens not only on the surface of the cavity, but also in the dentinal tubules. A further advantage is that the tubule structure is not modified or denatured here, as is frequently the case with the current procedures using dentin protecting agents and impregnating agents. The microbe-free conditions achieved in this way have a permanent beneficial effect on prosthetic procedures since dentin hypersensitivities and subsequently secondary caries are effectively avoided.

The application of the compounds of formula (I) or formula (II) can either replace or complement the disinfecting treatment with hydrogen peroxide. The compounds of formula (I) or formula (II) can be applied in dissolved form or as a gel, optionally in the presence of solubilizers to promote a deep penetration of the chemotherapeutic agents into the dentinal tubules. Gels are used in the provisional care of dentin wounds and solutions are preferably used before the definitive fixing of e.g. crowns and bridges. The solutions or gels of the chemotherapeutic agents used are applied to the prepared dentin surfaces and gently rubbed in. Residues are then removed, for example with a cotton wool swab or air jet. Inlays, onlays, crowns or bridges can then be fixed. The compounds of formula (I) or formula (II) can be used in concentrations of 0.005 mg/ml to 200 mg/ml. Preferred concentrations are those ranging from 0.5 mg/ml to 150 mg/ml and particularly preferred concentrations are those ranging from 10 to 100 mg/ml.

Topical Treatment of the Infected Root Canal and the Periapical Region

In the conventional method normally used nowadays for the topical treatment of the infected root canal and the periapical region, failures can be expected if, after extensive infections of the pulp and hence of the root canal, the extremely difficult diagnosis was established incorrectly, In these cases pathogenic microbes are present in the lateral branches of the pulp, in the apical delta, in the periapical region and in the outer dentin layer of the pulp cavity. It is known that infected tissue cannot be completely removed with instruments in many of these canal regions because of the anatomical conditions. The diverse branches, for example an apical delta or lateral branches, and the medullary canals cannot normally be reached and prepared with instruments. The usual disinfectants are also often unsuccessful. A particularly difficult situation arises when the microbes have advanced beyond the root canal aperture (foramen apicale). This periapical region cannot be reached with root canal instruments or disinfectants in the form of root canal inserts.

In the conventional treatment, the pulp, is removed with a nerve needle and the canal is prepared using root canal cutting instruments. This is to be understood as meaning the widening of the canal lumen and the removal of the infected canal wall. The mechanical preparation is combined with the use of chemical agents. The definitive root filling is carded out after completion of this treatment.

It has now been found, surprisingly, that the compounds of formula (I) or formula (II) can also be used for the topical treatment of the infected root canal and the periapical region. It was found that the compounds of formula (I) or formula (II) destroy all the microbes occurring in the root canal and in the periapical region, including those in all the mechanically inaccessible branches of the root canal and beyond the root tip in the periapical region. No bacterial resistances were found when using the compounds of formula (I) or formula (II). This behaviour of the compounds of formula (I) or formula (II) makes it possible to dispense with an extensive preparation in the form practised hitherto.

In the clinical use of the compounds of formula (I) or formula (II), the pulp residues are removed first. The preparation of the canals is carried out with minimum discomfort for the patient. The canals are then flushed with hydrogen peroxide, Other methods of disinfection can be omitted. The compounds of formula (I) or formula (II), in a liquid form of administration, are then introduced into the toot canal under pressure using a cannula. The compounds of formula (I) or (II) are then injected in dissolved form or in a gelatinous form of administration. The root canal is subsequently occluded in the crown region, first with a cotton wool plug and then with zinc phosphate cement to seal the margins. If the canals are not gangrenous, the antibiotics remain in the canals for 3 days. If the canals are gangrenous, it has proved advantageous to renew the application for a further three days. This treatment results in a successful therapy of infected root canals and of the apical region. The compounds of formula (I) or formula (II) can be used in concentrations of 0.005 mg/ml to 200 mg/ml. Preferred concentrations are those ranging from 0.5 mg/ml to 150 mg/ml and particularly preferred concentrations are those ranging from 10 to 100 mg/ml.

Topical application to the root canal can also advantageously be complemented by the local injection of a solution of the compounds of formula (I) or formula (II) into the periodontal interstice. In this application technique, which is known from intraligamental anaesthesia, the tooth is completely flooded with the antibacterial solution of the compounds of formula (I) or formula (II) in the entire root region. This effectively destroys the microbes which have invaded the periodontal interstice and the periapical region. Preferred forms of administration of the intraligamental injection are solutions of the compounds of formula (I) or formula (II) in concentrations of 0.005 mg/ml to 200 mg/ml. Preferred concentrations are those ranging from 0.5 mg/ml to 150 mg/ml and particularly preferred concentrations are those ranging from 1 to 100 mg/ml.

One particular advantage of using the compounds of formula (I) or formula (II) is that it is possible to preserve teeth which in the past often had to be extracted or on which a root tip resection had to be performed. The consequential costs, e.g. of preparing a dental prosthesis, can be expected to fall markedly.

Topical Treatment of Periodontal Diseases

Periodontal diseases are often the consequence of poor oral hygiene and in many cases are completely cured by local procedures, e.g. tartar removal. However, the success depends on the pocket depth and on whether the pathogenic microbes can be removed by supragingival scaling. If this treatment procedure is not successful, combination with the local application of antibiotics is recommended. The usual procedure is the local application of tetracyclines by means of threads. These ate pushed into the gingival pocket for several days. The advantage of this method is that an operative intervention can be avoided in many cases.

It has now been found, surprisingly, that the compounds of formula (I) or formula (II) are also suitable for the treatment of periodontal diseases. To do this, threads or so-called chips impregnated with solutions or gelatinous preparations of the compounds of formula (I) or formula (II) are inserted in the gingival pocket. A possible alternative is to use medicament carriers in the form of trays covering the teeth and gingiva. Before they are applied, the gelatinous applications of the compounds of formula (I) or formula (II) are instilled into the gingival pockets. In addition, the gel containing the compounds of formula (I) or formula (II) can also be placed in the medicament carrier. This use of medicament carriers is advantageous because the treatment time can be reduced by the rapid onset of action to about 15 to 30 minutes, so the treatment can be carried out directly in the surgery. The compounds of formula (I) or formula (II) can be used in concentrations of 0.005 mg/ml to 200 mg/ml. Preferred concentrations are those ranging from 0.5 mg/ml to 200 mg/ml and particularly preferred concentrations are those ranging from 10 to 150 mg/ml.

Periodontal diseases can also be treated by administering the compounds of formula (I) or formula (II) by intraligamental injection, it being possible to use concentrations ranging from 0.005 mg/ml to 200 mg/ml, preferably from 0.5 mg/ml to 200 mg/ml. For the antibiotics commonly used nowadays, such as tetracyclines, an intraligamental injection is not reasonable since these compounds with a predominantly bacteriostatic action are quickly washed out due to the rapid fluid exchange in the periodontal interstice, and cannot develop their action. Tetra-cyclines can therefore only develop their effects via depot formulations. By contrast, the compounds of formula (I) or formula (II) have a very rapid and also bactericidal action, so their residence time in the periodontal interstice is sufficient to destroy the microbes.

The treatment procedures were characterized by being very effective in that they covered the entire bacterial spectrum involved in periodontal diseases. The cure rates were very high. As a rule, the Treatment procedure was also markedly quicker than those conventionally used hitherto. Satisfactory clinical results were generally obtained after only the third rest period. The prospects of success of this novel method of treating periodontal diseases have been substantially improved by the use of compounds of formula (I) or formula (II). In many cases this approach can avoid an operative intervention.

It was found, surprisingly, that when the compounds of formulae (I) and (II) were applied to the gingival pocket, the gingival tissue regenerated very rapidly, reached a firm consistency and no longer bled. Accordingly, the topical and/or local application of the compounds of formulae (I) and (II) leads to a rapid regeneration of the periodontal tissues. This in turn leads to a rapid regrowth of the tooth-supporting tissues and a reattachment of the teeth.

Topical Treatment of Osseomucosal Wounds

Bacterial infections of the bone and soft tissues in the mouth and jaw region and in the face often have odontogenous causes. The origin is usually pulp-dead teeth, root residues, odontogenous cysts, dentitio difficilis and progressive periodontal diseases, Odontogenous abscesses are usually exposed surgically and drained until the cause has been eliminated. The various infections in the oral region require different therapeutic procedures. Thus it is generally possible to dispense with a systemic chemotherapy, for example in the case of infections near alveolar processes, whereas e.g. the treatment of phlegmons always requires the systemic administration of antibiotics. As a rule, however, combination with the topical application of antibiotics is advisable.

It has been found that the compounds of formula (I) or formula (II) can also be used for the topical treatment of osseomucosal wounds, having a beneficial effect on the therapy. Topical use of the compounds of formula (I) or formula (II) normally effects a rapid subsidence of the inflammatory symptoms and an early onset of healing. It has been observed that the healing process normally occurs much more rapidly than in the methods in common use today. The compounds of formula (I) or formula (II) thus have an extremely positive effect, i.e. accelerating effect, on the wound healing process.

Application is effected by flushing and/or by means of strip inserts impregnated with compounds of formula (I) or formula (II). They are to be used for example for postoperative infections following dentosurgical interventions (extractions). For this purpose the gel containing the compound of formula (I) or formula (II) is syringed directly into the extraction wound or onto a collagen sponge which remains in the extraction wound. The wound is closed for about half an hour by biting on a tampon. Prophylactic applications have been particularly successful after the extraction of teeth with focal infections, Liquid forms of administration suitable for flushing fistulae are those containing the compounds of formula (I) or formula (II) in concentrations of 0.005 mg/ml to 250 mg/ml. Preferred concentrations are those ranging from 0.5 to 100 mg/ml, Forms suitable for coating strips are gels containing the compounds of formula (I) or formula (II), as well as aqueous solutions or suspensions. These applications can contain the compounds of formula (I) or formula (II) in concentrations of 0.005 mg/ml to 200 mg/ml. Preferred concentrations for solutions are those ranging from 0.1 to 50 mg/ml Gelatinous forms of administration in concentrations of 25-150 mg/ml are preferred in the case of strip inserts.

Wound Care

Postoperative wound infections can generally occur in cases of inadequate infection prophylaxis following surgical interventions. Posttraumatic wound infections can arise due to cuts, stings, bruises, bites or gunshot wounds. Local perioperative prophylaxis can be carried out in the case of aseptic operations with a slight risk of infection. It is also possible to use local perioperative prophylaxis in addition to systemic perioperative prophylaxis, for example in the case of infections with an increased risk of infection, such as implantations, heart operations, transplantations, neurosurgical operations, operations in a highly contaminated area such as the oral cavity, oesophagus, rectum or colon, hysterectomy, bile duct operations, operations on patients with lowered resistance, or amputations. The local treatment of first, second or third degree burns can be administered prophylactically or after infection. Antibacterial local treatment is of great benefit especially in the case of severe burns. Examples of hand infections are panaritium cutaueum, panaritium subcutaneum, panaritium ossale, panaritium articulate or tendovaginitis purulenta. In postoperative sepsis the infected wounds can be rendered substantially or completely free of microbes by the topical application of antibacterial agents. Gangrenes can be handled by local treatment with antibiotics in addition to therapy with parenteral antibiotics. Examples of acute bacterial skin infections are pyoderma, erysipelas, furuncles, carbuncles, phlegmons, abscesses, ulcus cruris, diabetic foot, infected decubital ulcers, blood blisters, erysipeloids or erytlrasma. Examples of chronic bacterial skin infections are lupus vulgaris, swimming-pool granuloma, Buruli ulcers or actinomycosis. Secondary bacterial infections occur for example in virus infections such as herpes simplex, herpes zoster or chicken-pox. Secondary bacterial infections of dermatoses occur for example in eczema, the exudation stage of neurodermatitis, vesicular dermatoses or contact dermatitis. Milder and moderate forms of acne and rosacea can also be treated locally. In all the cases mentioned, local application of the compounds of formula (I) or formula (II) can be used either on its own or in addition to systemic application.

Local application of the compounds of formula (I) or formula (II) has proved advantageous because the broad efficacy of these compounds also makes it possible to treat mixed infections. Previous topical antibiotics have only a restricted spectrum of action and hence are less effective. Another advantage of the compounds of formula (I) or formula (II) is the very rapid onset of the antibacterial action. This allows a therapeutic response while the patient is still in the surgery. These compounds of formula (I) or formula (II) have an excellent bactericidal action and hence are superior to the current topical antibiotics, which often have only a bacteriostatic action and accordingly have to be used much more frequently and for much longer periods. Another advantage of the compounds of formula (I) or formula (II) compared with current local antibiotics is their good tissue penetration. Their penetration through the intact skin also allows the successful local treatment of deeper skin infections. The fact that the compounds of formula (I) or formula (II) have a considerably lower potential than conventional local antibiotics for the generation of bacterial resistance is to be regarded as a further advantage. This enables them to be used much more safely Another advantage of the compounds of formula (I) or formula (II) is a generally observable accelerating effect on wound healing. An additional advantage of the local use of compounds of formula (I) or formula (II) is the prevention of complications such as lymaphangitis, sepsis or chronic local infections.

Surprisingly, topical application of the compounds of formula (I) or formula (II) has also proved particularly effective in the therapy of diabetic foot syndrome. According to current medical practice, any lesion found to have local inflammation, with or without signs of systemic infection, demands immediate treatment with a broad-spectrum antibiotic. It has to be taken into account here that the inflammatory process normally involves a mixed infection with Gram-positive and Gram-negative microbes and with anaerobes and aerobes. Initially, the systemic administration of amoxicillin, clavulanic acid or clindamycin, each in combination with a gyrase inhibitor, proved effective. According to the result of the wound smear taken prior to the administration of antibiotics, the antibiosis can then be targeted. However, the time required for antibiotic therapy, especially in the case of osteomyelitic defects, is the subject of controversial discussion. The systemic administration of high doses of antibiotics for a period of months seems pointless if the X-ray examination shows no detectable tendency of the osteolysis to heal; a surgical intervention will become unavoidable in such a case.

In the therapy currently used for diabetic foot, an essential prerequisite for a cure without complications is a wound free of infection, Therefore, if the wound is infected, rapid and reliable treatment of the infection is of the highest priority. A local or systemic antibiotic therapy involves the risk of allergy and the development of resistance. Dressings consisting of active charcoal and elemental silver have proved particularly satisfactory, Non-toxic elemental silver controls local infection very effectively. Active charcoal binds microorganisms and cell detritus and makes it possible to remove the unwanted particles when the dressing is changed. Local irritations or allergies and the development of resistance are excluded and the necessary moist environment is assured at the same time. In modern wound treatment, dyes, with the exception of PVP/iodine complexes, are no longer important as disinfectants. Potassium permanganate has dosage problems and can cause severe skin burns. Ethacridine lactate has a high allergy rate and only a limited antimicrobial efficacy. Merbromin, which contains mercury, is highly toxic, impairs granulation and has disposal problems. Other dyes, e.g. brilliant green, methyl violet and fuchsin, are obsolete because of their low efficacy and especially because of their damaging effect on the epithelium.

Accordingly, in the current state of the aft, the treatment of diabetic foot is also in need of topical and/or local antibiotics which have a high activity against the microbes occurring in wounds, have a rapid action, have a good local tolerability, elicit a low tendency to generate antibiotic resistance, are easy to administer topically and/or locally, place a minimum system burden on the organism when applied topically/locally, have a good tissue penetration, are also suitable for the treatment of deep infections and furthermore accelerate the wound healing process.

It has now been found that topical application of the compounds of formula (I) or formula (II) can also achieve a satisfactory outcome in the therapy of diabetic foot syndrome. This was demonstrated particularly by the fact that, in patients with severe microangiopathies of the feet accompanying diabetic foot syndromes, attempted systemic treatments with Avalox 400 (moxifloxacin) and/or Clont 400 (2-methyl-5-nitro-1H-imidazol-1-ethanol) brought no significant changes in findings since these active ingredients were only able to achieve very low tissue concentrations after systemic administration because of pronounced micro-angiopathies. Surprisingly, however, topical application of the compounds of formula (I) or formula (II) led to significant improvements in the pathological process. Ulcers of different degrees of severity (D I to D V ulcers) could be treated. Greasy ulcers became clean, encrusted and smaller in size and even healed completely. This treatment was successful after several topical applications of the compounds of formula (I) or formula (II) at weekly intervals, said compounds being applied to the wound directly in dissolved form or, for example, as a gel or by means of impregnated compresses or dressings. These compounds of formula (I) or formula (II) can be applied to the wound in concentrations of 0.005 mg/ml to 200 mg/ml, preferred concentrations for solutions or gels being those ranging from 0.1 to 150 mg/ml. In the case of impregnated compresses or dressings, gelatinous forms of administration can be used in concentrations of 25-150 mg/lm.

It has further been found that local and/or topical application of the compounds of formula (I) or formula (II) is also beneficial in veterinary medicine. Recent studies have shown that, in many countries, two-thirds of dogs and more than 80% of cats over four years of age require dental treatment. Moreover, more than 10% of cats and 7,5% of dogs over 4 years of age suffer from severe periodontitis, which can lead to renal, hepatic and cardiac infections. It has now been found, surprisingly, that the compounds of formula (I) or formula (II) are also suitable for the treatment of dental diseases in animals. Endodontal treatments can be carried out using the same methods and the same active ingredient concentrations of the compounds of formula (I) or formula (II) as those explained above for treatments in human dental medicine. For the treatment of periodontal diseases, threads impregnated with solutions or gelatinous preparations of the compounds of formula (I) or formula (II) are inserted in the animal's gingival pocket. An alternative possibility is to use silicone trays. The compounds of formula (I) or formula (II) can be used in concentrations of 0.005 mg/ml to 200 mg/ml. Preferred concentrations are those ranging from 0.5 mg/ml to 200 mg/ml and particularly preferred concentrations are those ranging from 10 to 150 mg/ml.

When foreign bodies are introduced into the oral region of an animal for a prolonged period of time, reaction episodes can ensue, so it is often advantageous to treat periodontal diseases with compounds of formula (I) or formula (II) by direct instillation into the gingival pocket, by intraligamental injection or by means of a medicament carrier, for example a silicone tray. In the last case the animal to be treated is anaesthetized and a lump of workable silicone impression material, as conventionally used in human dental medicine, is pressed against the upper jaw. After the mouth has been closed, an impression of the lower teeth is made and) by pressing the still plastic material, the entire marginal regions of the gingiva are covered so as to overlap in the buccal cavity. After curing, the total impression of the upper and lower teeth and the gingival areas is removed and a compound of formula (I) or formula (II) is instilled into the gingival pockets and optionally placed in the cavities of the impression. The mould is placed on the animal's jaws again. The mouth is kept closed for after 15 to 30 minutes, allowing the compounds of formula (I) or formula (II) to make topical contact with the tissue, Topical and/or local application of the compounds of formulae (I) and (II) effects a rapid destruction of the bacteria and a rapid regeneration of the periodontal tissues. This leads to a rapid regrowth of the tooth-supporting tissues and a reattachment of the teeth. A further advantage of this method of treatment is that the animal's strong mouth odour is effectively and causally controlled. The compounds of formula (I) or formula (II) can be used as solutions or gels in concentrations ranging from 0.005 mg/ml to 200 mg/ml, preferably from 0.5 mg/ml to 200 mg/ml.

The compounds of formula (I) or formula (II) can also be used in combination with other anti-infective agents such as antibacterial, antifungal or antiviral substances.

The compounds of formula (I) or formula (II) can be used in concentrations of 0.005 mg/ml to 200 mg/ml. Preferred concentrations axe those ranging from 0.5 mg/ml to 200 mg/ml and particularly preferred concentrations are those ranging from 10 to 150 mg/ml.

The compounds of formula (I) or formula (II) can be used as solutions, gels, suspensions, emulsions or liposomes or in micelles. Examples of solutions are aqueous solutions in the presence of solubilizers. Examples of solubilizers are salts, polyols, sugar alcohols, polyglycols or co-solvents such as glycerol, ethylene glycol, propylene glycol, furfural, N,N-dimethylformamide, methanol, ethanol, i-propanol, n-propanol or acetone. Aqueous gels are prepared by the addition of gelling agents such as pectins, ethylene glycol monomethacrylate gel, alginates, hydroxyethyl cellulose, carboxymethyl hydroxyethyl cellulose, polyglyceryl methacrylates or polysaccharides. Other suitable additives are thickeners such as cellulose, alkyl cellulose, hydroxyethyl cellulose, agar-agar, carboxymethyl guar and cellulose ethers, or hydrotropic solubilizers such as ethylenediamine, urea or cyclodextrins. The galenical forms can also contain solubilizers such as surfactants, or preservatives. Examples of possible suspension constituents are tragacanth, cellulose, wetting agents, glycols, polyols, mucins or cellulose ethers. Possible emulsion constituents are emulsifiers such as polysorbates, surfactants, lecithins, mucins, gelatin or carboxymethyl cellulose. Other suitable forms of administration are dental pocket inserts consisting of an inert corner material, which are impregnated with the active ingredient and optionally other auxiliary substances and gradually release the active ingredient by dissolution. Examples of possible forms of administration for root fillings are tampons, cotton wool plugs or foam pellets. Application in the case of soft tissue infections can be effected with strips or thread inserts. It is also possible to use pharmaceutical substances or auxiliary substances for osmotic adjustment. Other possible auxiliary substances for formulating the compounds of formula (I) or formula (II) are antioxidants, chelating agents, disinfectants, dispersants, emulsion stabilizers, hydrocolloids, preservatives, solubilizers, wetting agents, quaternary ammonium compounds, stabilizers, suspending agents or thickeners. The above-mentioned constituents can also be used in combination with one another.

Suitable stable gelatinous formulations are those which, apart from the compounds of formula (I) or formula (II), ale composed of polyethers, modified celluloses and water. Preferred gel formulations are those containing the compounds of formula (I) or formula (II) in mixtures of propylene glycol, Tween 20 solution and muc. hydroxyethyl cellulose. Preferred compositions consist of compounds of formula (I) or formula (II) in amounts of 0.001 to 100 mg/ml, polypropylene glycol in amounts of 5 to 250 mg/ml, 1% Tween 20 solution in amounts of 5 to 200 mg/ml and muc. hydroxyethyl cellulose ad 1 g/ml. Particularly preferred gelatinous formulations consist of the compounds of formula (I) or formula (H) in amounts of 1 to 100 mg/ml, propylene glycol in amounts of 50 to 200 mg/ml, 1% Tween 20 solution in amounts of 3 to 150 mg/ml and muc. hydroxy cellulose ad 1 g/ml.

The Examples which follow serve to illustrate the present invention without however limiting the general spirit of the invention.

EXAMPLES

Examples of different formulations

Example 1:
Moxifloxacin · HCl solution

| | |
|---|---|
| moxifloxacin hydrochloride | 500 mg |
| aqua pro injectione | ad 100 ml |

Example 2:
High-viscosity formulation: moxifloxacin · HCl gel

| | |
|---|---|
| moxifloxacin hydrochloride | 1.0 g |
| hydroxyethyl cellulose | 0.5 g |
| propylene glycol | 1.5 g |
| distilled water ad | 10.0 g |

Example 3:
Low-viscosity formulation with stabilizer:
moxifloxacin · HCl gel

| | |
|---|---|
| moxifloxacin hydrochloride | 1.0 g |
| hydroxyethyl cellulose | 0.25 g |
| propylene glycol | 1.5 g |
| 1% Tween 20 solution | 1.0 g |
| distilled water ad | 10.0 g |

Example 4;
Moxifloxacin · HCl gel

| | |
|---|---|
| moxifloxacin hydrochloride | 0.1 g |
| hydroxyethyl cellulose | 0.25 g |
| propylene glycol | 1.5 g |
| 1% Tween 20 solution | 1.0 g |
| distilled water ad | 10.0 g |

A. Endodontal Diseases

A.1. Topical Treatment of Pulpitis Due to Carious Diseases

Patient A 1.1 (male, 43 years). Clinical diagnosis: tooth 24, mesial carious defect (enamel/dentin), tooth vital, increased sensitivity to cold. Course of treatment: removal of caries. Residual dentin covering very slightly softened. Pellet insert impregnated with moxifloxacin hydrochloride gel (25 mg/ml), provisional cavity occlusion. Check-up after 4 days: patient was symptom-free. Relining with dropsin, final filling with composite. Check-up after 3 weeks; tooth vital, patient symptom-free.

Patient A 1.2 (male, 33 years). Clinical diagnosis teeth 11, 13, major distal and mesial carious defects (enamel/dentin), all teeth vital, tooth 11 sensitive to cold, tooth 13 slightly sensitive to heat. Course of treatment: removal of caries Residual dentin covering hard. Pellet inserts with moxifloxacin hydrochloride gel (50 mg/ml), provisional cavity occlusion. Check-up after 1 week: teeth 11 and 13 symptom-free. Relining with dropsin, final filling with composite. Check-up after 14 days: teeth vital, patient symptom-free.

Patient A 1.3 (female, 18 years). Clinical diagnosis: tooth 24, major distal carious defect (enamel/dentin), tooth vital, sensitive to cold, sweet and sour. Course of treatment: removal of caries. Residual dentin covering hard. Pellet insert with moxifloxacin hydrochloride gel (25 mg/ml), provisional cavity occlusion. Check-up after one week: still slight discomfort of unknown origin, repetition of insert. Check-up after 3 days: tooth vital, patient symptom-free, Relining with dropsin, final filling with glass ionomer.

Patient A 1.4 (male, 23 years). Clinical diagnosis; tooth II, major mesial carious defect, tooth vital, sensitivity to heat and cold, night pain. Course of treatment: removal of caries. Residual dentin covering slightly softened. Pellet inserts wit moxifloxacin hydrochloride gel (50 mg/ml), provisional cavity occlusion. Check-up after 7 days: patient symptom-free, tooth vital. Relining with zinc phosphate cement, final filling with glass ionomer.

Patient A 1.5 (male, 43 years). Clinical diagnosis: tooth 13, major distal carious defect, tooth weakly vital, sensitivity to cold, night pain Course of treatment; removal of caries. Residual dentin covering hard. Pellet insert with moxifloxacin hydrochloride gel (50 mg/ml), provisional cavity occlusion. Check-up after 4 days, patient symptom-free, tooth vital. Relining with dropsin, final filling with composite.

Patient A 1.6 (female, 42 years). Clinical diagnosis: toot 36, major mesial carious defect, tooth with reduced vitality, sensitivity to cold and heat, night pain. Course of treatment: removal of caries, pellet insert with moxifloxacin hydrochloride gel (50 mg/ml), provisional cavity occlusion. Check-up after 6 days: still slight sensitivity to heat and cold, Repetition of insert. Check-up after 7 days: patient symptom-free, tooth vital. Relining with zinc phosphate cement, final filling with composite.

Patient A 1.7 (female, 18 years). Clinical diagnosis: tooth 44, major mesial carious defect, tooth with reduced vitality, sensitivity to cold, night pain. Course of treatment: removal of caries. Residual dentin covering slightly softened. Pellet inserts with moxifloxacin hydrochloride get (50 mg/ml), provisional cavity occlusion. Check-up after 4 days: patient symptom-free, relining with zinc phosphate cement, final filling with composite.

Patient A 1.8 (male, 38 years). Clinical diagnosis: tooth 36, major distal carious defect, tooth with reduced vitality, sensitivity to cold, heat, sweet and sour, slightly sensitive to percussion, night pain. Course of treatment: removal of caries. Residual dentin covering slightly softened. Pellet insert with moxifloxacin hydrochloride gel (50 mg/ml), provisional cavity occlusion, Check-up after 3 weeks: patient symptom-free, tooth vital, relining with zinc phosphate, final filling with composite.

Patient A 1.9 (female, 50 years). Clinical diagnosis, tooth 27, major distal carious defect, tooth vital, sensitivity to cold, slight sensitivity to heat, slight night pain. Course of treatment: removal of caries. Residual dentin covering softened. Pellet insert with moxifloxacin hydrochloride gel (25 mg/ml), provisional occlusion. Check-up after 7 days: patient symptom-free, tooth vital, Patient A 1.10 (male, 17 years). Clinical diagnosis: teeth 16, 17, 27, 36, 37, 46 with occlusal caries, teeth vital, sensitivity to cold, sweet and sour, sometimes to heat, not localizable. Course of treatment: removal of caries. Residual dentin coverings hard. Pellet inserts with moxifloxacin hydrochloride gel (50 mg/ml), provisional cavity occlusion, Check-up after 14 days, patient symptom-free, teeth vital. Relining with dropsin, final filling with composite.

Patient A 1.11 (male, 33 years). Clinical diagnosis: tooth 22, distal carious defect (enamel/dentin), tooth vital, slight sensitivity to heat. Course of treatment: removal of caries, residual dentin covering very slightly softened. Pellet insert impregnated with grepafloxacin gel (25 mg/ml), provisional cavity occlusion, Check-up after 5 days: patient was symptom-free. Refining with zinc phosphate cement, final filling with composite. Check-up after 4 weeks: tooth vital, patient symptom-free.

Patient A 1.12 (male, 38 years), Clinical diagnosis: teeth 22, 23 with major distal carious defects (enamel/dentin), teeth vital, sensitivity to cold. Course of treatment: removal of caries, residual dentin covering hard. Pellet inserts with grepafloxacin gel (50 mg/ml), provisional cavity occlusion.

Check-up after 1 week: teeth symptom-free. Relining with dropsin, final filling with composite. Check-up after 14 days: teeth vital, patient symptom-free.

Patient A 1.13 (female, 48 years). Clinical diagnosis: tooth 14, major mesial carious defect (enamel/dentin), tooth vital, sensitivity to cold and sour. Course of treatment: removal of caries, residual dentin covering hard. Pellet insert with gemifloxacin mesylate gel (25 mg/ml), provisional cavity occlusion. Check-up after 3 weeks, still slight discomfort. Repetition of insert, Check-up after 4 days: tooth vital, patient symptom-free. Relining with dropsin, final filling with glass ionomer.

Patient A 1.14 (male, 53 years). Clinical diagnosis: tooth 13, major mesial carious defect, tooth vital, sensitivity to heat, night pain. Course of treatment: removal of caries, residual dentin covering slightly softened. Pellet inserts with levofloxacin gel (50 mg/ml), provisional cavity occlusion, Check-up after 14 days: patient symptom-free, tooth vital. Relining with dropsin, final filling with composite.

Patient A 1.15 (male, 22 years). Clinical diagnosis tooth 44, major mesial carious defect, tooth vital, sensitivity to cold, night pain. Course of treatment: removal of caries, residual dentin covering leathery. Pellet insert with trovafloxacin mesylate gel (50 mg/ml), provisional cavity occlusion. Check-up after 9 days: patient symptom-free, tooth vital. Relining with dropsin, final filling with composite.

Patient A 1.16 (female, 15 years). Clinical diagnosis: tooth 46, major distal carious defect, tooth with reduced vitality, sensitivity to cold and heat. Course of treatment: removal of caries, pellet insert with sparfloxacin gel (25 mg/ml), provisional cavity occlusion. Check-up after 4 days: still slight sensitivity to heat. Repetition of insert. Check-up after 14 days: patient symptom-free, tooth vital. Relining with dropsin, final filling with composite.

A.2. Prophylaxis of Dentin Wounds

Patient A 2.1 (male, 30 years). Clinical diagnosis: teeth 33 and 36, carious defects on both teeth. Teeth vital. Course of treatment: preparation of teeth 33 and 36. Make-up of provisional bridge. Application of moxifloxacin hydrochloride solution (25 mg/ml) to cavity, drying in gentle air jet. Fixing of bridge with provisional cement. After 8 days, definitive insertion of bridge with zinc phosphate cement. Check-up after 3 weeks: patient symptom-free.

Patient A 2.2 (male, 48 years). Clinical diagnosis teeth 22, 23, 24 with small distal carious defects (enamel/dentin), all teeth vital, sensitivity to cold. Course of treatment: removal of caries, smear with moxifloxacin hydrochloride solution (50 mg/ml), provisional cavity occlusion. Check-up after 2 weeks: teeth symptom-free Relining with dropsin, final filling with composite Check-up after 4 weeks: teeth vital, patient symptom-free.

Patient A 2.3 (female, 28 years). Clinical diagnosis: teeth 14, 15, 16, 17 with cervical erosions (enamel/dentin), sensitivity to cold and sweet. Course of treatment: preparation, smear with moxifloxacin hydrochloride solution (50 mg/m), gentle drying in air jet. Adhesive restoration with composite. Check-up after 3 weeks: patient symptom-free.

Patient A 2.4 (male, 33 years). Clinical diagnosis: teeth 11, 12, 21, 22 with carious defects in first third of dentin, teeth vital, Course of treatment: preparation for ceramic crowns. Smear with moxifloxacin hydrochloride solution (25 mg/ml), drying in gentle air jet, insertion of provisional crowns. After 14 days, insertion of definitive crowns with zinc phosphate cement. Check-up after 3 weeks: patient symptom-free.

Patient A 2.5 (male, 62 years). Clinical diagnosis: tooth 44, mesial carious defect in first third of dentin, sensitivity to cold. Course of treatment: removal of caries, smear with moxifloxacin hydrochloride solution (25 mg/ml), provisional cavity occlusion. Check-up after 9 days: patient symptom-free. Relining with dropsin, final filling with composite.

Patient A 2.6 (female, 18 years). Clinical diagnosis: tooth 43, distal carious defect in first third of dentin. Course of treatment: removal of caries, smear with moxifloxacin hydrochloride solution (25 mg/ml), relining with dropsin, final filling with composite. Patient failed to attend check-up, Patient A 2.7 (female, 28 years). Clinical diagnosis: teeth 15, 14, 13, 12, 11, 21, 22, 23, 24, 25 with cervical erosions, severe hypersensitivity. Course of treatment: cleaning of eroded regions, smear with sparfloxacin solution (50 mg/ml), gentle drying in air jet. Adhesive restoration with composite.

Patient A 2.8 (female, 33 years). Clinical diagnosis: teeth 13, 14, 15 with mesial and distal carious defects in fist third of dentin, sensitivity to cold. Course of treatment: preparation of cavities, removal of caries, smear with trovafloxacin mesylate solution (25 mg/ml), drying in gentle air jet. Adhesive restoration with glass ionomer cement.

A.3. Topical Treatment of the Infected Toot Enamel and the Periapical Region

Patient A 3.1 (female, 40 years), Clinical diagnosis: tooth 45, apical periodontitis due to pulpitis purulenta, slight bite discomfort. Slightly widened periodontal interstice in X-ray, not gangrenous. Course of treatment: canal preparation down to apex. Canal insert with moxifloxacin hydrochloride solution (100 mg/ml) by syringe, then topping-up with moxifloxacin hydrochloride gel (100 mg/ml), provisional occlusion. Check-up after 3 days: patient symptom-See, root filling with endomethasone. Check-up after 14 days: patient still symptom-free, final filling with composite.

Patient A 3.2 (male, 70 years). Clinical diagnosis: tooth 23, gangrenous, bite discomfort X-ray normal, Course of treatment: canal preparation down to apex, canal insert with moxifloxacin hydrochloride solution (100 mg/ml) by syringe, then topping-up with moxifloxacin hydrochloride gel (100 mg/ml), provisional occlusion. Check-up after 14 days: patient symptom-free, canal odourless. Root filling with endomethasone.

Patient A 3.3 (female, 22 years). Clinical diagnosis: tooth 11, apical periodontitis due to gangrene, bite discomfort. Widened periodontal interstice in X-ray. Course of treatment: canal preparation down to apex, canal insert with moxifloxacin hydrochloride solution (50 mg/ml) by syringe, then topping-up with moxifloxacin hydrochloride gel (50 mg/ml) and intraligamental injection of moxifloxacin hydrochloride solution (50 mg/ml). Provisional occlusion. Check-up after 3 days: patient symptom-free, canal odourless, Patient A 3.4 (male, 40 years). Clinical diagnosis: tooth 11, apical periodontitis due to pulpitis purulenta, not gangrenous, bite discomfort, Widened periodontal interstice in X-ray. Course of treatment: canal preparation down to apex, root canal insert with moxifloxacin hydrochloride gel (50 mg/ml), provisional occlusion. Check-up after 3 days: patient symptom-free. Root filling with endomethasone, provisional occlusion. Check-up after 3 weeks: patient still symptom-free. Final filling with composite.

Patient A 3.5 (female, 43 years). Clinical diagnosis: tooth 35, apical periodontitis due to gangrene, slight bite discomfort. Weak translucence visible in X-ray Course of treatment: canal preparation down to apex not possible. Root canal insert wilt moxifloxacin hydrochloride solution (50 mg/ml) by syringe, then topping-up with moxifloxacin hydrochloride gel (50 mg/ml) and intraligamental injection of moxifloxacin hydrochloride solution (50 mg/ml). Check-up after 7 days: no gangrenous odour, no bite discomfort. Root filling with N2 medical. Check-up after 7 days: patient symptom-free. Final filling with composite.

Patient A 3.6 (male, 29 years). Clinical diagnosis: tooth 36, apical periodontitis due to gangrene, bite discomfort. X-ray normal, Course of treatment: canal preparation down to apex, root canal insert with moxifloxacin hydrochloride gel (50 mg/ml) and intraligamental injection of moxifloxacin hydrochloride solution (50 mg/ml). Check-up after 8 days: no gangrenous odour, patient symptom-free Root filling with N2 medical. Check-up after 3 weeks: patient symptom-free. Final filling with composite.

Patient A 3.7 (female, 50 years). Clinical diagnosis: tooth 14, apical periodontitis due to gangrene. Slight bite discomfort. Weak translucence in X-ray. Course of treatment: canal preparation down to apex, root canal insert wilt moxifloxacin hydrochloride gel (100 mg/ml) and intraligamental injection of moxifloxacin hydrochloride solution (50 mg/ml), provisional occlusion. Check-up after 7 days: patient symptom-free. Root filling with endomethasone. Check-up after 3 weeks: patient still symptom-free. Final filling with composite.

Patient A 3.8 (female, 42 years). Clinical diagnosis: tooth 34, apical periodontitis due to gangrene, bite discomfort. Weak translucence visible in X-ray. Course of treatment: canal preparation down to apex not possible, Root canal insert with moxifloxacin hydrochloride gel (50 mg/ml) and intraligamental injection of moxifloxacin hydrochloride solution (50 mg/ml), provisional occlusion. Check-up after 13 weeks: patient symptom-free, canal odour-free. Root filling with endomethasone, final filling with glass ionomer.

Patient A 3.9 (female, 17 years). Clinical diagnosis: tooth 46, apical periodontitis due to pulpitis purulenta, slight bite discomfort, tooth not gangrenous. Slightly widened periodontal interstice at mesial root in X-ray. Course of treatment: canals prepared down to apex, root canal insert with moxifloxacin hydrochloride gel (100 mg/ml) and intraligamental injection of moxifloxacin hydrochloride solution (50 mg/ml). Checkup after 7 days; patient symptom-free. Root filling with endomethasone, final filling. Patient failed to attend subsequent check-up.

Patient 3.10 (female, 24 years). Clinical diagnosis tooth 14, fistula in root tip region, tooth gangrenous. Slight bite discomfort. Course of treatment: canal preparation down to apex. Canal and fistula flushed with moxifloxacin hydrochloride solution (50 mg/ml) by syringe, canal insert with moxifloxacin hydrochloride gel (50 mg/ml) and intraligamental injection of moxifloxacin hydrochloride solution (50 mg/ml). Canal occluded only with cotton wool plug. Check-up after 3 days: patient still not completely symptom-free. Canal still had very slight gangrenous odour. Repetition of flushing with moxifloxacin hydrochloride solution (50 mg/ml) and canal insert with moxifloxacin hydrochloride gel (50 mg/ml). Check-up after 8 days: patient symptom-free. Root filling with endomethasone. Check-up after 3 weeks; patient symptom-free. Final filling with composite.

Patient A 3.11 (male, 51 years), Clinical diagnosis: tooth 34, apical periodontitis due to pulpitis purulenta, not gangrenous, no bite discomfort. Fistula in root tip region. Weak translucence in X-ray. Course of treatment: canal preparation down to apex not possible at palatinal root. Root canal insert with moxifloxacin hydrochloride gel (100 mg/ml), provisional occlusion. Check-up after 10 days: patient symptom-free. Root filling with endomethasone. Patient failed to attend check-up.

Patient A 3.12 (female, 34 years). Clinical diagnosis: tooth 44, fistulation, bite difficulties, gangrenous. Course of treatment canal preparation down to apex. Root canal insert with moxifloxacin hydrochloride solution (50 mg/ml) using paper point and intraligamental injection of moxifloxacin hydrochloride solution (50 mg/ml), provisional occlusion. Check-up after 8 days; patient symptom-free. Root filling with endomethasone, final filling with composite.

Patient A 3.13 (female, 78 years). Clinical diagnosis: tooth 15, apical periodontitis due to pulpitis purulenta, slight bite discomfort, not gangrenous. Course of treatment: canal preparation down to apex, canal insert with moxifloxacin hydrochloride solution (50 mg/ml) by syringe and then topping-up with moxifloxacin hydrochloride gel (50 mg/ml) and intraligamental injection of moxifloxacin hydrochloride solution (50 mg/ml), provisional occlusion. Check-up after 9 days: patient symptom-free, root filling with endomethasone. Check-up after 10 days: patient still symptom-free, final filling with composite.

Patient A 3.14 (male, 30 years). Clinical diagnosis: tooth 13, gangrenous, bite discomfort, X-ray normal. Course of treatment: canal preparation down to apex, canal insert with moxifloxacin hydrochloride solution (50 mg/ml) by sage and then topping-up with moxifloxacin hydrochloride gel (50 mg/ml) and intraligamental injection of moxifloxacin hydrochloride solution (50 mg/ml), provisional occlusion. Check-up after 10 days: patient symptom-free, canal odourless, root filling with endomethasone.

Patient A 3.15 (female, 32 years). Clinical diagnosis: tooth 31, apical periodontitis due to gangrene, bite discomfort, widened periodontal interstice in X-ray. Course of treatment: canal preparation down to apex, canal insert with moxifloxacin hydrochloride solution (50 mg/ml) by syringe, then topping-up with moxifloxacin hydrochloride gel (50 mg/ml) and intraligamental injection of moxifloxacin hydrochloride solution (50 mg/ml), provisional occlusion. Check-up after 9 days: patient symptom-free, canal odourless.

Patient A 3.16 (male, 40 years). Clinical diagnosis: tooth 46, apical periodontitis due to pulpitis purulenta, not gangrenous, widened periodontal interstice visible no X-ray. Course of treatment: canal preparation down to apex, root canal insert with grepafloxacin gel (50 mg/ml), provisional occlusion. Check-up after 3 weeks: patient symptom-free. Root filling with endomethasone, provisional occlusion Check-up after 1 week; patient still symptom-free, final filling with composite.

Patient A 3.17 (female, 33 years). Clinical diagnosis: tooth 32, apical periodontitis due to gangrene, slight bite discomfort, weak translucence visible in X-ray. Course of treatment: canal preparation down to apex not possible, Root canal insert with grepafloxacin solution (20 mg/ml) by syringe, then topping-up with grepafloxacin gel (20 mg/ml) and intraligamental injection of grepafloxacin solution (50 mg/ml). Check-up after 6 days: no gangrenous odour, no bite discomfort. Root filling with N2 medical. Check-up after 4 days: patient symptom-free. Final filling with composite.

Patient A 3.18 (female, 55 years). Clinical diagnosis: tooth 34, apical periodontitis due to gangrene, slight bite discomfort, weak translucence visible in X-ray. Course of treatment: canal preparation down to apex, root canal insert with trovafloxacin mesylate gel (100 mg/ml) and intraligamental injection of trovafloxacin mesylate solution (50 mg/ml), provisional occlusion. Check-up after 12 days: patient symptom-free. Root filling with endomethasone. Check-up after 3 weeks: patient still symptom-free. Final filling with composite.

Patient A 3.19 (female, 22 years). Clinical diagnosis: tooth 11, apical periodontitis due to gangrene simplex. Course of treatment: canal preparation down to apex not possible. Root canal insert with trovafloxacin mesylate solution (50 mg/ml), provisional occlusion. Check-up after 3 weeks: patient symptom-free, canal odour-free. Root filling with endomethasone, final filling with glass ionomer.

Patient A 3.20 (female, 77 years). Clinical diagnosis: tooth 47, apical periodontitis due to pulpitis purulenta, tooth not gangrenous, slightly widened periodontal interstice at mesial root visible in X-ray. Course of treatment; canals prepared down to apex. Root canal insert with tosufloxacin tosylate gel (100 mg/ml). Check-up after 8 days; patient symptom-free. Root filling with endomethasone, final filling. Patient failed to attend subsequent check-up Patient A 3.21 (female, 54 years), Clinical diagnosis tooth 22, fistula in root tip region, tooth gangrenous, slight bite discomfort. Course of treatment: canal preparation down to apex, canal and fistula flushed with moxifloxacin hydrochloride solution (50 mg/ml) by syringe, canal insert with moxifloxacin hydrochloride gel (50 mg/ml) and intraligamental injection of moxifloxacin hydrochloride solution (50 mg/ml). Canal occluded only with cotton wool plug. Check-up after 8 days: patient still not fully symptom-free, canal still had very slight odor, Repetition of flushing and insert. Check-up after 10 days; patient symptom-free. Root filling with endomethasone. Check-up after 1 week: patient symptom-free. Final filling with composite.

Patient A 3.22 (male, 50 years). Clinical diagnosis: tooth 35, apical periodontitis due to pulpitis purulenta, not gangrenous, no bite discomfort. Course of treatment; canal preparation down to apex, root canal insert with tosufloxacin tosylate gel (50 mg/ml), provisional occlusion. Check-up after 10 days: patient symptom-free. Root filling with endomethasone, Patient failed to attend check-up.

Patient A 3.23 (female, 64 years). Clinical diagnosis: toot 34, fistulation, bite difficulties, gangrenous Course of treatment: canal preparation down to apex, root canal insert with grepafloxacin solution (50 mg/ml) using paper point, intraligamental injection of grepafloxacin solution (50 mg/ml), provisional occlusion. Check-up after 10 days: patient symptom-free. Root filling with endomethasone, final fill-in with composite.

B. Topical Treatment of Periodontal Diseases

Patient B 1 (female, 33 years). Clinical diagnosis: teeth 26 and 27, marginal periodontitis with exposed root cement, pocket depths of 4 to 5 run, strong foetor ex ore. Course of treatment: removal of concrement by ultrasound and manually, thread insert with moxifloxacin hydrochloride gel (50 mgn/ml). Covering with Gingipac gingival dressing. Check-up after 3 days: patient symptom-free, gingival regions and pockets inflammation-free.

Patient B 2 (female, 60 years). Clinical diagnosis: teeth 14 to 18, severe marginal periodontitis with exposed root cement, pocket depths of 5 to 6 mm. Course of treatment: removal of concrement by ultrasound, thread insert with moxifloxacin hydrochloride gel (50 mg/ml), covering with Gingipac gingival dressing. Check-up after 4 days, patient symptom-free, gingival regions and pockets inflammation-free.

Patient B 3 (male, 49 years). Clinical diagnosis teeth 24 to 28, marginal periodontitis with exposed root cement, pocket depths of 4 to 6 mm. Course of treatment: removal of concrement by ultrasound and manually, thread insert with moxifloxacin hydrochloride (50 mg/ml), covering with Gingipac gingival dressing Check-up after 5 days: patient symptom-free, gingival regions and pockets inflammation-free.

Patient B 4 (female, 20 years). Clinical diagnosis: marginal periodontitis in entire upper and lower jaw region, strong foetor ex ore, pocket depths of 4 to 5 mm. Course of treatment: removal of concrement by ultrasound, medicinal splint with moxifloxacin hydrochloride gel (0.25 mg/ml) worn for 10 minutes/day for 4 days. Check-up after 3 days: patient symptom-free, no more inflammatory phenomena present.

Patient B 5 (female, 53 years) Clinical diagnosis: tooth 37, marginal periodontitis with exposed root cement, pocket depths of 5 mm, strong foetor ex ore. Course of treatment; removal of concrement by ultrasound and manually, thread insert with moxifloxacin hydrochloride gel (50 mg/ml), covering with Gingipac gingival dressing. Check-up after 8 days: patient symptom-free, gingival regions and pockets inflammation-free.

Patient B 6 (female, 30 years). Clinical diagnosis teeth 25-28, severe marginal periodontitis with exposed root cement, pocket depths of 4 mm. Course of treatment: removal of concrement by ultrasound, thread insert with moxifloxacin hydrochloride gel (50 mg/ml), intraligamental injection of moxifloxacin hydrochloride solution (50 mg/ml), covering with Gingipac gingival dressing Check-up after 10 days: patient symptom-free, gingival regions and pockets inflammation-free.

Patient B 7 (male, 35 years). Clinical diagnosis: teeth 14-17, marginal periodontitis with exposed root cement, pocket depths of 4 mm. Course of treatment: removal of concrement by ultrasound and manually, thread insert with grepafloxacin gel (50 mg/ml), intraligamental injection of grepafloxacin solution (50 mg/ml), covering with Gingipac gingival dressing, Check-up after 9 days: patient symptom-free, gingival regions and pockets inflammation-free.

Patient B 8 (female, 33 years). Clinical diagnosis: marginal periodontitis in entire upper and lower jaw region, strong foetor ex ore, pocket depths of 3-5 mm. Course of treatment: removal of concrement by ultrasound, medicinal splint with trovafloxacin mesylate gel (0.25 mg/ml) worn for 10 minutes/day for 6 days. Check-up after 6 days: patient symptom-free, inflammation phenomena no longer present.

C. Topical Treatment of Osseomucosal Wounds

Patient C 1 (male, 14 years). Clinical diagnosis: teeth 011 and 012, wound care after extraction, reimplanted teeth. Course of treatment: resorption, ankylosis and sequestrum in X-ray. Excochleation after wound care. Application of depot of moxifloxacin hydrochloride gel (50 mg/ml) by gauze strip. Check-up after 3 days: patient symptom-free, good wound margin adaptation.

Patient C 2 (male, 16 years). Clinical diagnosis: regio 36, wound care after major surgical interventions, slight submucosal swelling, fistulation on tooth 36 following pulpitis purulenta. Course of treatment: incision, flushing with moxifloxacin hydrochloride solution (50 mg/ml), strip insert with moxifloxacin hydrochloride gel (50 mg/ml). Check-up after 3 days: patient symptom-free, good rapid healing process, Patient C 3 (female, 34 years). Clinical diagnosis: teeth 26 and 46 with apical granulomas, severe bite discomfort. Course of treatment: extraction at inflammatory stage (osteotomy), no suture. Wound care with gauze impregnated with moxifloxacin hydrochloride gel (50 mg/ml). Check-up after 2 days: patient symptom-free.

Patient C 4 (female, 34 years). Clinical diagnosis: tooth 48, impacted and displaced. Course of treatment: wound care following major surgical intervention (osteotomy), wound care with gauze impregnated with moxifloxacin hydrochloride gel (50 mg/ml). Wound closure with two button sutures. Check-up after 2 days: slight wound pain, no postoperative oedema. Check-up after one week: removal of sutures, good wound margin adaptation, patient symptom-free.

Patient C 5 (male, 52 years). Clinical diagnosis: tooth 34, pulpitis purulenta, fistulation, submucosal swelling. Course of treatment: trepanation, incision, flushing of root canal and fistula with moxifloxacin hydrochloride solution (50 mg/ml), canal insert with moxifloxacin hydrochloride gel (50 mg/ml), completion only with cotton wool plug, gauze insert impregnated with moxifloxacin hydrochloride gel (50 mg/nil) in affected region, no suture. Check-up after 3 days: good healing process, patient symptom-free. Root canal filling with endomethasone. Check-up after 3 weeks: patient symptom-free.

Patient C 6 (male, 44 years). Clinical diagnosis: tooth 36, wound care after extraction. Course of treatment dolor post, restoration of alveolus, application of depot of moxifloxacin hydrochloride gel (50 mg/ml) by gauze strips. Check-up after 3 days: patient symptom-free, good wound margin adaptation.

Patient C 7 (male, 36 years). Clinical diagnosis: tooth 22, wound care following root tip resection due to cyst. Course of treatment: incision, strip insert with moxifloxacin hydrochloride gel (50 mg/ml). Check-up after 3 days: patient symptom-free, good healing process.

Patient C 8 (female, 31 years). Clinical diagnosis: teeth 26 and 26 with apical granulomas, bite discomfort. Course of treatment: extraction at inflammatory stage (osteotomy), wound care with gauze impregnated with grepafloxacin gel (50 mg/ml). Check-up after 3 days: patient is symptom-free, Patient C 9 (male, 22 years), Clinical diagnosis: tooth 14, pulpitis purulenta, fistulation, submucosal swelling. Course of treatment; trepanation, incision. Flushing of root canal and fistula with moxifloxacin hydrochloride solution (25 mg/ml), canal insert with grepafloxacin gel (25 mg/ml), completion only with cotton wool plug. Gauze insert impregnated with moxifloxacin hydrochloride gel (25 mg/ml) in affected region, no suture. Check-up after 6 days: patient symptom-free, Root canal filling with endomethasone. Check-up after 2 weeks, patient symptom-free, D. Wound Care Patient D 1 (male, 33 years). Diagnosis: combustio escharotica on left forearm. Course of treatment: wound hygiene, application of moxifloxacin hydrochloride gel (1%), wound covering. Regeneration of skin epithelium with complete wound closure after one week, Patient D 2 (male, 25 years). Diagnosis: panaritium parunguale on right middle finger. Course of treatment: conduction anaesthesia, opening at nail margin, local antibiosis with moxifloxacin hydrochloride gel (1%), insertion of rubber flap. Patient symptom-free.

Patient D 3 (male, 70 years), Diagnosis: diabetes mellitus, hospital stay due to severe diabetic microangiopathy of the feet with diabetic foot syndrome Then outpatient foot care. Findings: a) deep, 2×1.5 cm ulcer under right big toe, greasy, b) large ulcer D III, 5 m diameter; c) large fissure D IV/D V; severe keratinization of entire foot. Course of treatment: attempted systemic treatment with Avalox 400 and Clont 400 without significant change in findings. Then application of dressings with moxifloxacin hydrochloride gel (1%) at weekly intervals. Wound check-up after 1st week: a) ulcer D I, 1×0.5 cm, clean; b) ulcer D III clean; c) ulcer D IV/D V encrusted. Wound check-up after 2nd week: a) ulcer D I pinhead-size, clean, b) ulcer D III, clean granular tissue; c) ulcer C IV/D V healed. Wound check-up after 3rd week: a) ulcer D I unchanged; b) ulcer D III pinhead-size. Wound check-up after 4th week: a) ulcer D I healed; b) ulcer D III healed.

Patient D 4 (male, 62 years). Diagnosis: diabetes mellitus, diabetic microangiopathy of right foot with diabetic foot syndrome. Findings, 1×1 cm ulcer, greasy; severe keratinization of entire foot. Course of treatment; application of dressings with moxifloxacin hydrochloride gel (1%) at weekly intervals. Wound check-up after 1st week: ulcer 0.2×0.4 cm, clean. Would check-up after 2nd week: ulcer healed.

Patient D 5 (female, 67 years). Diagnosis: diabetic gangrene on left big toe. Course of treatment: wound hygiene, removal of hyperkeratosis and necrosis, Four applications of moxifloxacin hydrochloride gel (1%) at weekly intervals, covering wound each time. Regeneration of skin epithelium with complete wound closure, revascularization.

Patient D 6 (male, 34 years). Diagnosis; erysipelas on right lower leg. Course of treatment; immobilization, local antibiosis with moxifloxacin hydrochloride gel (1%), local compresses. After 2 days, prevention of recurrence. Patient symptom-free.

Patient D 7 (female, 52 years). Diagnosis: phlegmons on palm of left hand. Course of treatment, incision and wide opening of affected tissue areas, local antibiosis with moxifloxacin hydrochloride gel (1%), wound care. After 2 days, repetition of local antibiosis. Patient symptom-free.

Patient D 8 (female, 28 years). Diagnosis: furuncle oil left forearm. Course of treatment: incision and open wound treatment with moxifloxacin hydrochloride solution (1%) Patient symptom-free.

Patient D 9 (female, 44 years). Diagnosis: carbuncle on back of neck, Course of treatment: excision of all necrotic areas, open wound treatment with moxifloxacin hydrochloride-impregnated compress. Patient symptom-free.

What is claimed is:

1. A method for the treatment of periodontal diseases in a subject in need thereof, said method comprising topically and/or locally administering to periodontal pocket of said subject a therapeutically effective amount of a medicament selected from the group consisting of moxifloxacin and/or its corresponding hydrate and/or its corresponding physiologically compatible acid addition salt.

2. The method according to claim 1, wherein the moxifloxacin is in the form of an acid addition salt selected from the group consisting of hydrochloride, hydrobromide, methanesulfonate and toluenesulfonate.

3. The method according to, claim 1 wherein the medicament is in the form of a gel, a solution, a suspension, an emulsion, liposomes or micelles and has optionally been applied to or incorporated in a carrier material or an inert carrier.

4. The method according to claim 3, wherein the medicament is in the form of an aqueous solution.

5. The method according to claim 3, wherein the medicament contains a physiologically compatible auxiliary substance selected from the group consisting of solvents, thickeners, solubilizers, preservatives, emulsifiers, mucins, osmolality regulators, antioxidants, chelating agents, disinfectants, dispersants, emulsion stabilizers, hydrocolloids, wetting agents or a mixture of at least two of the above-mentioned auxiliary substances.

6. The method according to claim 3 wherein the medicament is in the form of a strip insert, thread insert, chip, tray, collagen sponge, tampon, cotton wool plug or foam pellet.

7. The method according to claim 1, wherein the medicament is present in the form of a gel or a solution in a concentration of 0.005 mg/ml to 200 mg/ml.

8. The method according to claim 1 wherein the subject is selected from humans and animals.

9. A method for the treatment of periodontal diseases in a subject in need thereof, said method comprising topically administering to a periodontal pocket of said subject a therapeutically effective amount of a medicament selected from the group consisting of moxifloxacin and/or its corresponding hydrate and/or its corresponding physiologically compatible acid addition salt.

10. The method according to claim 7, wherein the medicament is a gel formulation comprising from 0.001 to 100 mg/mL moxifloxacin hydrochloride, about 1 g/mL hydroxyethyl cellulose, from 5 to 250 mg/mL propylene glycol, and water.

11. The method according to claim 10, wherein the gel formulation further comprises from 3 to 150 mg/mL Tween 20.

12. The method according to claim 1, wherein the therapeutically effective amount of the medicament ranges from 0.005 to 200 mg/mL.

13. The method according to claim 3, wherein the medicament is in the form of a pellet comprising a gel comprising from 0.001 to 100 mg/mL moxifloxacin hydrochloride, about 1_g/mL hydroxyethyl cellulose, from 5 to 250 mg/mL propylene glycol, and water.

14. The method according to claim 1, comprising administering moxifloxacin to an oral canal insert in the subject.

15. The method according to claim 14, further comprising administering moxifloxacin to the subject via intraligamental injection.

16. The method according to claim 14, wherein the oral canal insert is a root canal insert.

17. The method according to claim 1, wherein the medicament is in the form of a medicinal splint comprising from 0.001 to 100 mg/mL moxifloxacin hydrochloride, about 1 g/mL hydroxyethyl cellulose, from 5 to 250 mg/mL propylene glycol, and water.

18. The method according to claim 17, further comprising administering moxifloxacin in the form of a thread insert to the subject, and further comprising administering moxifloxacin to the subject via intraligamental injection.

* * * * *